(12) United States Patent
Gebert et al.

(10) Patent No.: US 6,214,992 B1
(45) Date of Patent: Apr. 10, 2001

(54) USE OF THEOPHYLLINE DERIVATIVES FOR THE TREATMENT AND PROPHYLAXIS OF STATES OF SHOCK, NOVEL XANTHINE COMPOUNDS AND PROCESSES FOR THEIR PREPARATION

(75) Inventors: Ulrich Gebert, Glashütten; Erhard Wolf, Hofheim; Elisabeth Defossa, Idstein; Uwe Heinelt; Hiristo Anagnostopulos, both of Wiesbaden; Karl Rudolphi, Mainz; John J. Grome, Wiesbaden, all of (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 08/868,641

(22) Filed: Jun. 4, 1997

(30) Foreign Application Priority Data

Jun. 7, 1996 (DE) ............................... 196 22 737
Jul. 24, 1996 (DE) ............................... 196 29 815

(51) Int. Cl.$^7$ ......................... A61K 31/52; C07D 473/04
(52) U.S. Cl. ............................................. 544/267
(58) Field of Search ............................................. 544/267

(56) References Cited

U.S. PATENT DOCUMENTS

| | | | |
|---|---|---|---|
| 4,904,472 | 2/1990 | Belardinelli et al. | 514/263 |
| 5,350,753 | 9/1994 | Klesel et al. | 514/264 |

FOREIGN PATENT DOCUMENTS

| | | |
|---|---|---|
| 0 462 506 A1 | 12/1991 | (EP) . |
| 0 771 813 A1 | 5/1997 | (EP) . |
| 3-167186 | 7/1991 | (JP) . |
| 8700532 | 1/1987 | (WO) . |

OTHER PUBLICATIONS

Daly, Pharmacology 42, 309, 1991.*
Ingo Marzi et al., "Influence of Pentoxifylline and Albifylline on Liver Microcirculation and Leukocyte Adhesion after Hemorrhagic Shock in the Rat", The Journal of Trauma: Injury, Infection and Critical Care, vol. 40, No. 1, pp. 90–96 (1996).
Eiichiro Okabe, "Preventive Effects of Theophylline on Anaphylactic Shock in Rats", Japan J. Pharmacol., vol. 30, pp. 367–376 (1980).
Burr Eichelman et al., "Methylxanthine–Facilitated Shock–Induced Aggression in the Rat", Psychopharmacology, vol. 56, pp. 305–308 (1978).
J.P. Tarayre et al., "Theophylline reduces Pulmonary *eosinophilia* after various types of active anaphylactic shock in guinea–pigs", J. Pharm. Pharmacol., vol. 43, pp. 877–879 (1991).
Kurt L. Berens et al., "Influence of Pentoxifylline and Related Analogues in Endotoxemic Renal Failure", Circulatory Shock, vol. 34, pp. 344–348 (1991).
P. Masouye et al., "Xanthine Derivative HWA 138 Attenuates Hemodynamic and Oxygen Uptake Dysfunction Secondary to Severe Endotoxin Shock in Sheep", Circulatory Shock, vol. 36, pp. 113–119 (1992).
von Roslindis, Bericht, Med Mo Pharm. 1989, 12/9, 279–82.
Taeger, Medwelt 1989, 40, 519–22.
Parrillo, Joseph E., N. Eng. Journ Med., 1993, 328/20, 1471–7.
Bone, Roger C.,J. Amer. Med. Assoc., 1992, 268, 3452.
K. Skarvan, Medwelt 1989, 40, 525–32.
John Davis, Scrip Magazine, Dec. 1994, 50–52.
Galanos et al.Proc. Nat'l Acad. Sci. USA 1979, vol. 76, p 5939–5943.
Barton, Beverly E., DN&P 1993, 6/9, 641–6.
Miyamoto et al., J. Med. Chem. 1993, 36/10, 1380–6.
Ridson et al.,Synth. Commun. 1990, 20, 2459–67.
Karger et al., J. Org. Chem. 1971, 36, 528–31.
Karger et al., J. Amer. Chem Soc., 1969, 91, p3663.
Rudolphi et al. J. Cereb. Blood Flow Metab. 1987, 7, p74–81.
Zhou et al., J. Cereb. Blood Flow Metab. 1994, 14, 166–173.
Pschyrembel,Klinisches Worterbuch, Walter de GruyterVerlag (1986) 1513.

* cited by examiner

Primary Examiner—Mark L. Berch
(74) Attorney, Agent, or Firm—Finnegan, Henderson, Farabow, Garrett & Dunner, L.L.P.

(57) ABSTRACT

Theophylline derivatives having at least one ether function in the structurally modified methyl radical in the 1-position that are useful in the treatment and prophylaxis of states of shock, new xanthine compounds having this substitution pattern, and processes for their preparation.

24 Claims, No Drawings

USE OF THEOPHYLLINE DERIVATIVES FOR THE TREATMENT AND PROPHYLAXIS OF STATES OF SHOCK, NOVEL XANTHINE COMPOUNDS AND PROCESSES FOR THEIR PREPARATION

DESCRIPTION

Use of theophylline derivatives for the treatment and prophylaxis of states of shock, novel xanthine compounds and processes for their preparation.

The present invention relates to the use of theophylline derivatives having at least one ether function in the structurally modified methyl radical in the 1-position for the production of pharmaceuticals for the treatment and prophylaxis of shock disorders, to new xanthine compounds having the above mentioned substitution pattern and to processes for their preparation.

Shock is defined as an acutely occurring condition of inadequate nutritive perfusion of vital organs, which always represents the highest danger to life (Med. Mo. Pharm. 1989, 12/9: 279–282).

The causes of shock are varied. Thus cardiogenic shock is caused by primary heart failure as a result of myocardial infarct, severe cardiac arrhythmias, cardiac muscle insufficiency or other cardiac disorders, of hypovolemic shock (hemorrhagic and traumatic shock and also burn and dehydration shock) due to fluid losses or displacements, of septic shock due to systemic infiltration of microbes (gram-negative and gram-positive bacteria, fungi, viruses, protozoa etc.) or their toxins and finally of anaphylactic shock due to generalized antigen-antibody reactions. Despite this variety of causes, however, the pathogenesis and clinical picture of the various forms of shock proves to be very uniform (Pschyrembel, klinisches Wörterbuch [Clinical dictionary], Walter de Gruyter-Verlag, 255th Edition, 1986, page 1513). A disorder of the cell functions always plays a key part as a result of inadequate supply of the tissue with oxygen and substrates (ischemia) and inadequate disposal of the toxic metabolic products (Medwelt 1989, 40: 519–522). Shock is a dynamic event whose course depends substantially on the duration of ischemia. In the first, compensated shock phase, the body reacts with a neuronally and hormonally controlled centralization of the circulation, by means of which the organs situated in the center of the body (heart, brain, lungs, liver, kidneys) are protected for the time being. The clinical picture is characterized by tachycardia, still normal or only slightly lowered blood pressure, hyperventilation with respiratory alkalosis and as a rule pale, cold and clammy skin; in septic shock fever also occurs, from time to time associated with shivering fits. If the compensation mechanisms are exhausted, the capillary perfusion of the central organs is also impaired to an increasing extent. This leads into the second, decompensated shock phase, which is characterized by progressive cell death and loss of function. The occurrence of shock is irreversible. The drastic increase in the vascular permeability in the microcirculation area leads through loss of fluid to a rise in the hematocrit, to interstitial edemas and to the release of mediators which, inter alia, cause a disseminated intravasal coagulation, for example in the form of a consumptive coagulopathy with obturating fibrin thrombi in the terminal vascular system. The constant reduction in cardiac output and blood pressure leads to complete circulatory collapse. At the end of the shock cascade death results due to acute failure of the heart, liver, kidneys or lungs (ARDS=Acute Respiratory Distress Syndrome) or due to multi-organ failure (MOF), if several organs simultaneously lose their function.

Conventional therapy is orientated to clinical symptomatology and includes immediate measures for eliminating the vital threat, such as volume substitution, artificial respiration for the prophylaxis of ARDS, administration of vasoactive pharmaceuticals to support the circulation, analgesia and sedation, correction of the disorders in the acid-based balance, heparin administration to avoid a consumptive coagulopathy and treatment with corticosteriods to reduce membrane permeability. Depending on the cause of shock, further therapeutic measures are indicated, for example operation and hemostasis in hemorrhagic shock, elimination of the focus of infection and antibiotic therapy in septic shock and possible treatment by means of cardiac pacemaker and aortal balloon counterpulsation in cardiogenic shock. In spite of all these therapeutic measures, the result of treatment, however, remains extremely unsatisfactory. Thus the mortality rates, for example, in cardiogenic shock on account of a cardiac infarct is 90% and in septic shock, the globally most frequent cause of death in intensive-care units, is more than 50%.

This makes understandable the demand by clinics for a more causally aligned therapy concept, which allows as early an interruption of the shock cascade as possible and thus distinctly improves the chance of survival. Promising starting points for this are offered by the complex pathophysiological processes which underlie the progressive course of the shock disorder. According to present knowledge, a number of mediator systems and inflammatorily competent cells are activated by the respective pathological stimulus both in septic and aseptic forms of shock (N. Engl. J. Med. 1993, 328/20: 1471–1477) and by this means an endothelial inflammation with diffuse inflammatory processes is caused, which is also designated (J. Amer. med. Ass. 1992, 268: 3452) as SIRS (Systemic Inflammatory Response Syndrome). At the center of this syndrome is the generalized pathological interaction between activated granulocytes and endothelial cells via complementary adhesion molecules which, with progressive vascular damage, leads to disorders in the microcirculation and organ damage with increasing functional impairment and finally ends up in a multi-organ failure. With triggering of the vascular wall-associated inflammatory processes by the granulocytic endothelial interaction, septic and aseptic events follow a common pathogenetic final route with the development of shock. Moreover, there are sound indications for the fact that in the course of aseptic forms of shock an invasion of bacteria or their toxic products into the blood stream described as bacterial translocation occurs via an initially nonmicrobally triggered barrier disorder in the lung and, in particular, gastrointestinal tract, so that aseptic and septic events overlap (Medwelt 1989, 40: 525–532).

More recent attempts at a causal therapeutic intervention now aim at specific interventions in the disease process supported by inflammatory mediators, in order to interrupt the pathological signal chain as early as possible and thus prevent the development of organ damage in time. In large-scale clinical studies, for example, murine and human monoclonal antibodies against the endotoxin (LP= Lipopolysaccharide) from the cell wall of gram-negative bacteria, humanized recombinant and both murine and human monoclonal antibodies against the cytokine TNF (tumor necrosis factor), soluble TNF receptors prepared by genetic engineering and other TNF binding proteins of the physiologically occurring interleukin-1 receptor antagonist Antril (IL-1-RA) produced by recombination as well as the bradykinin antagonist Bradycor have been investigated without a therapeutic breakthrough becoming apparent until now (Scrip Magazine, December 1994: 50–52). The intensive search for effective blockers of the extremely complex disease event therefore continues undiminished, the knowledge increasingly gaining acceptance that the switching-off of a specific mediator of the wide-ranging signal cascade only has low prospects of success and that therapeutic advances are most likely to be expected from a multifunctional intervention, be it just by combination of various selectively active pharmaceuticals or advantageously by a monopharmacon with as wide a pharmacological spectrum of action as possible.

For the testing of preparations for antishock action, various experimental animal models have been developed. A particularly practicable readily standardized and predictive model (Proc. Natl. Acad. Sci. U.S.A. 1979, 76/11: 5939–5943) is endotoxin lipoplysaccharide (LPS)-induced shock on C57BU6 mice, which realistically follows the clinical situation inasmuch as the sensitivity of the animals to LPS is so greatly increased by simultaneous administration of galactosamine (GaIN) that the comparatively low lethal dose in humans also suffices here for the triggering of the fatal shock event (DN&P 1993, 6/9: 641–646; Biospektrum 1995, 1/5: 46–52). In this model, theophylline (1,3-dimethylxanthine) shows no noticeable protective action at doses up to the tolerability limit.

Surprisingly, it has now been found that the introduction of substituents having at least one ether function into the methyl radical in the 1-position of the theophylline molecule produces very potent preparations with, at the same time, substantially improved tolerability. Three compounds of this structural type are known, namely the 3-n-propylxanthine having the 2-methoxyethy, 2-ethoxyethyl or 3-methoxypropyl group in the 1-position (J. Med. Chem. 1993, 36/10: 1380–1386), which on account of bronchodilatory properties ought to be suitable for the treatment of acute asthma attacks, but references to their utility as anti-shock agents do not exist.

The invention relates to the use of at least one compound of the formula I

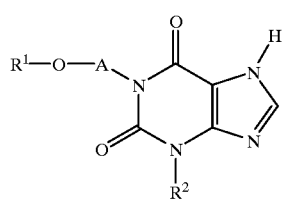

(I)

where
R$^1$ is
 a) straight-chain or branched ($C_1$–$C_5$)-alkyl,
 b) ($C_1$–$C_2$)-alkoxy-($C_1$–$C_3$)-alkyl or
 c) phenyl or phenyl-($C_1$–$C_2$)-alkyl, in which the phenyl radicals are unsubstituted or each substituted by one or two halogen atoms,
A is an unbranched or branched ($C_1$–$C_4$)-alkylene bridge and
R$^2$ is
 a) straight-chain or branched ($C_1$–$C_5$)-alkyl,
 b) ($C_3$–$C_6$)-cycloalkyl,
 c) ($C_4$–$C_8$)-cycloalkylalkyl,
 d) phenyl or
 e) phenyl-($C_1$–$C_2$)-alkyl,
for the production of a pharmaceutical for the treatment and prophylaxis of shock disorders, in particular of SIRS (Systemic Inflammatory Response Syndrome), sepsis, sepsis syndrome, septic shock, multi-organ failure (MOF), ARDS (Acute Respiratory Distress Syndrome), hemorrhagic and traumatic shock and also burn and dehydration shock and shock-like complications in the reperfusion syndrome and extracorporeal circulation.

Preferred compounds of the formula I employed are those where
R$^1$ is
 a) straight-chain or branched ($C_1$–$C_4$)-alkyl,
 b) methoxymethyl,
 c) methoxyethyl,
 d) phenyl,
 e) 4-chlorophenyl,
 f) benzyl or
 g) 4-chlorobenzyl,
A is an unbranched ($C_1$–$C_3$)-alkylene bridge and
R$^2$ is
 a) straight-chain or branched ($C_1$–$C_4$)-alkyl,
 b) cyclopropyl,
 c) cyclopropylmethyl,
 d) phenyl or
 e) benzyl.

Furthermore preferred is the use of the compounds of the formula 1, where
R$^1$ is straight-chain or branched ($C_1$–$C_4$)-alkyl,
A is an unbranched ($C_1$–$C_3$)-alkylene bridge and
R$^2$ is straight-chain or branched ($C_1$–$C_4$)-alkyl, cyclopropyl or cyclopropylmethyl.

The expression "($C_4$–$C_8$)-cycloalkylalkyl" defines those alkyl radicals which are substituted by ($C_3$–$C_6$)-cycloalkyl, where the sum of all carbon atoms is smaller than or equal to 8. These are the cyclopropylmethyl to -pentyl, cyclobutylmethyl to -butyl, cyclopentylmethyl to -propyl and cyclohexylmethyl and -ethyl radicals. Halogen atoms are iodine, bromine, fluorine and, preferably, chlorine.

The invention also relates to novel compounds of the formula I, in which
R$^1$ is
 a) straight-chain or branched ($C_1$–$C_5$)-alkyl,
 b) ($C_1$–$C_2$)-alkoxy-($C_1$–$C_3$)-alkyl or
 c) phenyl or phenyl-($C_1$–$C_2$)-alkyl, in which the phenyl radicals are unsubstituted or each substituted by one or two halogen atoms,
A is an unbranched or branched ($C_1$–$C_4$)-alkylene bridge and
R$^2$ is
 a) straight-chain or branched ($C_1$–$C_5$)-alkyl,
 b) ($C_3$–$C_6$)-cycloalkyl,
 c) ($C_4$–$C_8$)-cycloalkylalkyl,
 d) phenyl or
 e) phenyl-($C_1$–$C_2$)-alkyl,
where compounds of the formula I in which a) R$^2$ is n-propyl, R$^1$ is methyl or ethyl and A is an ethylene bridge or b) R$^2$ is n-propyl, R$^1$ is methyl and A is an n-propylene bridge are excluded.

Preferred compounds of the formula I are those in which
R$^1$ is
 a) straight-chain or branched ($C_1$–$C_4$)-alkyl,
 b) methoxymethyl,
 c) methoxyethyl,
 d) phenyl,
 e) 4-chlorophenyl,
 f) benzyl or
 g) 4-chlorobenzyl, A is an unbranched $(C_1-C_3)$-alkylene bridge and
$R^2$ is
  a) straight-chain or branched $(C_1-C_4)$-alkyl,
  b) cyclopropyl,
  c) cyclopropylmethyl,
  d) phenyl or
  e) benzyl,
where compounds of the formula I in which a) $R^2$ is n-propyl, $R^1$ is methyl or ethyl and A is an ethylene bridge or b) $R^2$ is n-propyl, $R^1$ is methyl and A is an n-propylene bridge are excluded.

Furthermore preferred compounds of the formula I are those in which
  $R^1$ is straight-chain or branched $(C_1-C_4)$-alkyl,
  A is an unbranched $(C_1-C_3)$-alkylene bridge and
  $R^2$ is straight-chain or branched $(C_1-C_4)$-alkyl, cyclopropyl or cyclopropylmethyl,
where the compounds of the formula I in which a) $R^2$ is n-propyl, $R^1$ is methyl or ethyl and A is an ethylene bridge or b) $R^2$ is n-propyl, $R^1$ is methyl and A is an n-propylene bridge are excluded.

The compounds of the formula I can be deprotonated in the 7-position and therefore form salts and solvates with basic agents. Those possible for this purpose are preferably pharmaceutically acceptable alkali metal and alkaline earth metal salts and the salts and solvates with organic bases, for example ethylenediamine, or the basic amino acids lysine, ornithine and arginine. The invention thus also relates to the physiologically tolerable salts and/or solvates of the 1,3-disubstituted xanthines of formula I and their use as active compounds in antishock compositions.

Compounds of the formula I having an unsymmetrically branched alkyl radical in the position of $R^1$ and/or $R^2$ and/or having an unsymmetrically branched alkylene bridge A have one or more asymmetric carbon atoms and can thus be present in stereoisomeric forms. The invention therefore includes both the stereoisomerically pure compounds and their mixtures, and their use as active compounds in antishock compositions.

The invention further relates to an analogous process for the preparation of the novel compounds of formula I, whose fundamental embodiments are described in WO 87/00523. For example, a procedure is thus used in which
a) a 3-substituted xanthine of the formula II

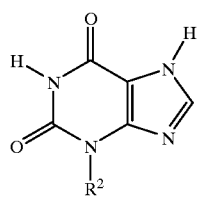

(II)

in which $R^2$ is as defined in formula I, is reacted without condensing agent or in the presence of a basic condensing agent or in the form of its salts with a reagent of the formulae III $$R^a-X \qquad (III)$$

in which $R^a$ is an easily eliminable leaving group, for example the reductively or alternatively hydrolytically removable benzyl, benzhydryl or trityl group, having unsubstituted or substituted phenyl rings, and X is halogen, preferably chlorine, bromine or iodine, or alternatively a sulfonic acid ester or phosphonic acid ester group, or
b) a 7-substituted xanthine of the formula IV

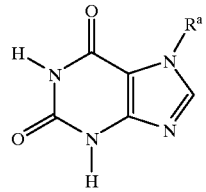

(IV)

in which $R^a$ is benzyl having an unsubstituted or substituted phenyl radical, is reacted without condensing agent or in the presence of a basic condensing agent or in the form of its salts with a reagent of the formula V $$R^2-X \qquad (V)$$

in which $R^2$ is as defined in formula I and X is as defined in formula III, to give a 3,7-disubstituted xanthine of the formula VI

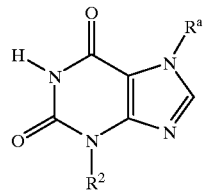

(VI)

in which $R^2$ is as defined in formula I and $R^a$ is as defined in formula III or IV, then the compound of the formula VI is converted without condensing agent or in the presence of a basic condensing agent or in the form of its salts, using an alkylating agent of the formula VII $$R^1-O-A-X \qquad (VII)$$

in which $R^1$ and A are as defined in formula I and X is as defined in formula III, into a 1,3,7-trisubstituted xanthine of the formula VIII

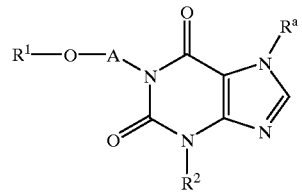

(VIII)

in which $R^1$, A and $R^2$ are as defined in formula I and $R^a$ is as defined in formula III or IV, and finally by elimination of the leaving group $R^a$ from the intermediate of the formula VII the compound of the formula I according to the invention is obtained and this is optionally converted, if appropriate after separation of the stereoisomeric forms, into a physiologically tolerable salt.

The monosubstituted xanthines of the formulae II and IV and alkylating agents of the formulae III, V and VII used in this context as starting substances are for the greatest part known or can be easily prepared by known methods. Thus, for example, the 7-benzylxanthines of the formula IV are accessible from guanosine by benzylation, hydrolytic elimination of the sugar radical and subsequent conversion of the guanosine structure into the xanthine structure (Synth. Commun. 1990, 20: 2459–2467). With the introduction of the $R^1$—O—A-side chain into the 1-position of the xanthine structure of suitable alkylating agents of the formula VII, those compounds in which A is a methylene group (A=—$CH_2$—) assume a special position inasmuch as their halides can admittedly be employed successfully as reactants, but at least on large-scale use can raise toxocological problems. Therefore, in this special case the use of the corresponding sulfonates may be preferred, which are conveniently accessible, for example, by reaction of mixed anhydrides of aliphatic carboxylic acids and of aliphatic or of aromatic sulfonic acids (J. Org. Chem. 1971, 36: 528–531) with the disubstituted formaldehyde acetals of the formula IX in a reaction which is clear and goes nearly to completion (J. Amer. Chem. Soc. 1969, 91: 5663–5665):

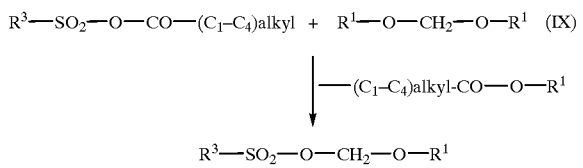

In this context, $R^3$ is an aliphatic radical such as methyl, ethyl or trifluoromethyl or an aromatic radical, for example phenyl, 4-tolyl or 4-bromophenyl, but preferably methyl or 4-tolyl, and $R^1$ has the meanings defined under formula I. The reaction can be carried out both in substance and in an anhydrous, aprotic solvent, which is inert to the reaction components, at temperatures between −20° and +40° C., preferably between 0° and 20° C. Intermediate isolation of the highly reactive sulfonates, which are sensitive to hydrolysis and heat-labile, is not necessary; they are expediently used directly as crude products for the alkylation of the xanthines VI on the nitrogen atom in the 1-position, the otherwise customary addition of a basic condensing agent often being unnecessary.

The reaction of the mono- and disubstituted xanthine derivatives II, IV and VI with the alkylating agents of the formula II, V or VII concerned is usually carried out in a diluent or solvent which is inert to the reaction participants. Those which are suitable are especially dipolar, aprotic solvents, for example dimethylformamide, dimethylacetamide, N-methylpyrrolidone, tetramethylurea, hexamethylphosphoramide or dimethyl sulfoxide; it is also possible to use, however, formamide, acetonitrile, acetone, butanone or alcohols, such as methanol, ethylene glycol and its mono- or di($C_1$–$C_4$)alkyl ethers, ethanol, propanol, isopropanol and the various butanols; hydrocarbons, such as benzene, toluene or xylene; halogenated hydrocarbons, such as dichloromethane or chloroform; pyridine as well as mixtures of the solvents mentioned or mixtures thereof with water. The alkylation reactions are expediently carried out in the presence of a basic condensing agent. Those suitable for this purpose are, for example, alkali metal or alkaline earth metal hydroxides, carbonates, hydrides, alkoxides and organic bases, such as trialkylamines, e.g. triethyl- or tributylamine, quaternary ammonium or phosphonium hydroxides and crosslinked resins having attached, optionally substituted ammonium or phosphonium groups. The xanthine derivatives, however, can also be employed directly in the form of their separately prepared salts, for example the alkali metal, alkaline earth metal or optionally substituted ammonium or phosphonium salts. Furthermore, the xanthine compounds can be conveniently alkylated both in the presence of the abovementioned inorganic condensing agents and in the form of alkali metal or alkaline earth metal salts with the assistance of so-called phase-transfer catalysts, for example tertiary amines, quaternary ammonium or phosphonium salts or alternatively crown ethers, preferably in a two-phase system under the conditions of a phase-transfer catalysis. Suitable, mostly commercially available phase-transfer catalysts are, inter alia, tetra(($C_1$–$C_4$)alkyl- and methyltrioctylammonium and phosphonium, methylmyristyl-, phenyl and benzyl-tri($C_1$–$C_4$)alkyl- and cetyltrimethylammonium and also ($C_1$–$C_{12}$)alkyl- and benzyltriphenyl-phosphonium salts, as a rule those compounds which have the cation of larger and more symmetrical construction proving to be more effective. In the procedures described above, the reaction is in general carried out at a reaction temperature of between 0° C. and the boiling point of the reaction medium used in each case, preferably between 20° and 130° C., optionally at elevated or reduced pressure, but usually at atmospheric pressure, it being possible for the reaction time to be from less than one hour up to several hours.

The elimination of the leaving group $R^a$ from the compounds of the formula VIII with formation of the xanthines of the formula I according to the invention is carried out under standard conditions, which were developed especially in the context of the protective group technique in alkaloid and peptide syntheses and can thus be assumed to be largely known.

The benzyl, benzhydryl or trityl group which is optionally substituted in the phenyl rings is then preferably reductively eliminated. Beside chemical reduction, in particular of the benzyl compounds with sodium in liquid ammonia, the elimination of the three abovementioned aralkyl groups by catalytic hydrogenolysis with the aid of a noble metal catalyst is preferably suitable here, the substitution of molecular hydrogen by ammonium formate as a hydrogen donor having proven suitable. The reaction medium used here is usually a lower alcohol, optionally with addition of formic acid or alternatively ammonia; an aprotic solvent, such as dimethylformamide; or, in particular, glacial acetic acid; however, mixtures thereof with water can also be used. Suitable hydrogenation catalysts are especially palladium black and palladium on activated carbon or barium sulfates, while other noble metals, such as platinum, rhodium and ruthenium often give rise to side reactions on account of competing nuclear hydrogenation and can therefore only be employed to a limited extent. The hydrogenolysis is expediently carried out at temperatures between 20° and 100° C. and under atmospheric pressure or preferably a slight overpressure of up to about 10 bar, as a rule reaction times of a few minutes up to several hours being needed. Alternatively, however, the elimination of the protective group $R^a$, such as, for example, of the 4-methoxybenzyl, benzhydryl or trityl radical, can also be carried out hydrolytically with customary proton catalysis.

The preparation of the compounds of the formula I according to the invention in stereoisomerically pure form is preferably carried out by subsequent separation of the stereoisomeric forms with the aid of methods known per se. As diastereomers, in contrast to enantiomers, have different physical and chemical properties, the separation of mixtures thereof, for example by fractional crystallization or chromatographic processes, generally presents no difficulties. On the other hand, physical resolution of racemates into the enantiomeric forms (antipodes) requires additional precautions; thus fractional crystallization takes place only after formation of diastereomeric salts using an optically active base and chromatographic separation only when using chiral stationary phases which exhibit a different spatial affinity for the enantiomers.

The 1,3,7-trisubstituted xanthines of the formula VIII are useful intermediates for the preparation of the compounds of the formula (I) according to the invention, and moreover, in particular if $R^a$ is benzyl, already show the same pharmacological trend of action as the final products of the formula I and therefore also belong to the claim range of the present invention, even though they are more difficult to administer parenterally on account of their lower water solubility.

The novel compounds of the formula I according to the invention are outstandingly suited on account of their useful pharmacological properties for use as active compounds in pharmaceuticals, in particular in those which permit an effective curative and prophylactic treatment of shock disorders and thus are a substantial enrichment of pharmaceutical wealth. They can either be administered per se, for example in the form of microcapsules, in mixtures with one another or in combination with suitable excipients.

The invention therefore also relates to pharmaceuticals which contain at least one compound of the formula I, the 3-n-propylxanthines having 2-methoxyethyl, 2-ethoxyethyl or 3-methoxypropyl in the 1-position and previously described as active compounds for pharmaceuticals having another indication being excluded.

A further aspect of the present invention is the use of the compounds of the formula I for the production of pharmaceutical preparations for parenteral and oral administration, but optionally also rectal administration, transdermal administration or administration by inhalation in shock disorders. Suitable solid or liquid pharmaceutical preparation forms are, for example, granules, powders, tablets, coated tablets, (micro)capsules, syrups, emulsions, suspensions, gels, preparations with delayed release of active compound, suppositories, active compound-releasing patches, aerosols, drops and especially injectable solutions in the form of ampoules or injection bottles for continuous infusion, in whose preparation auxiliaries, such as excipients, disintegrants, binders, coating agents, swelling agents, glidants or lubricants, flavorings, sweeteners or solubilizers are customarily used. Frequently used auxiliaries which may be mentioned are, for example, magnesium carbonate, titanium dioxide, lactose, mannitol and other sugars, talc, lactoprotein, gelatin, starch, vitamins, cellulose and its derivatives, animal and vegetable oils, polyethylene glycols and solvents, such as, for example, sterile water, physiological saline solution, alcohols, glycerol and other polyhydric alcohols (polyols).

Preferably, the pharmaceutical preparations are prepared and administered in dose units, each unit containing as active constituent a specific dose of a compound of formula I. In the case of solid dose units, such as tablets, capsules and suppositories, this dose can be up to 1000 mg, but preferably 100 to 600 mg, and in the case of injection solutions in ampoule form up to 300 mg, but preferably 20 to 200 mg.

For the treatment of an adult patient—depending on the activity of the compounds of formula I in man and the degree of severity of the life-threatening disorder—daily doses of 100 to 5000 mg of active compound, preferably 300 to 3000 mg, are indicated in the case of oral administration and of 30 to 3000 mg, preferably 50 to 2000 mg, in the case of intravenous administration. The administration of the daily dose can be carried out either by single administration in the form of an individual dose unit or, however, of several small dose units, or by repeated administration of subdivided doses at specific time intervals.

In the case of intravenous continuous infusion, the daily dose is 100 to 5000 mg, preferably 500 to 2000 mg, corresponding to an infusion rate of 0.1 to 3 mg per kg of body weight per hour (h), preferably of 0.3 to 1 mg/kg/h.

In the case of all administration forms, however, under certain circumstances higher or lower daily doses may be appropriate.

Finally, the compounds of the formula I—if clinically indicated—can also be administered together with other suitable active compounds, in particular with those which also intervene in a regulating manner in the signal cascade of the shock event; for example with antibodies against entero- and endotoxins (LPS), the monocytic LPS receptor CD14 or the LPS-binding protein LBP; with modulators of the cytokine network such as anti-TNF antibodies, soluble TNF receptors and other TNF-binding proteins, inhibitors of interleukin-1 (IL-1) and/or TNF production and/or release, and TNF and IL-1 receptor antagonists; with inhibitors of arachidonic acid metabolism and of the coagulation and complement cascade such as phospholipase $A_2$, cyclooxygenase and lipoxygenase inhibitors (e.g. steroids and non-steroidal antiinflammatories such as ibuprofen), PAF (platelet-activating factor), leukotriene, thromboxane, thrombin, fibrin, bradykinin and serotonin antagonists and also anti-C5a or -C3a antibodies; with anticoagulants and platelet aggregation inhibitors such as antithrombin III, tissue plasminogen activator tPA-1, heparin and also prostacyclin and its more stable synthetic derivatives; with inhibitors of the release and/or of the biological action of lytic enzymes; with oxygen radical scavengers such as superoxide dismutase, catalase, alpha-tocopherol or N-acetylcysteine; with heavy metal chelators such as deferoxamine; with inhibitors of intercellular adhesion such as fibronectin or antibodies against the adhesion molecules ELAM-1, ICAM-1, VCAM-1 and CD11/CD18; or else alternatively with antibiotics, or are formulated together in the preparation of the abovementioned pharmaceutical preparation forms.

Below, the synthesis of the compounds of formula I compiled according to structural points of view in Table 1 is explained in greater detail with the aid of representative preparation examples. In Table 2, the useful intermediate compounds of the formula VIII are compiled in the same arrangement. For all synthetically prepared intermediates and final products, the structure was confirmed both by $^1$H-NMR spectroscopy and by elemental analysis or mass spectrum.

PREPARATION EXAMPLES

Example 1

1-Methoxymethyl-3-methylxanthine (compound 1)

a) 7-Benzyl-3-methylxanthine 20 g (0.5 mol) of sodium hydroxide dissolved in 200 ml of water were added to a suspension of 83 g (0.5 mol) of 3-methylxanthine in 500 ml of methanol and the reaction mixture was stirred at 70° C. for one hour, then treated dropwise at the same temperature with 85.5 g (0.5 mol) of benzyl bromide and kept between 700 and 800 for 5 hours. The mixture was then cooled and filtered cold on a suction filter, the product was washed with water on the suction filter and dissolved hot in 1000 ml of 1N sodium hydroxide solution, filtered and slowly brought to pH 9.5 using 4N hydrochloric acid with stirring. The crystallizate was filtered off from the still warm solution, washed with water until chloride-free and dried in a vacuum drying oven overnight. Yield: 81.7 g (63.8% of theory); melting point: 263° C. $C_{13}H_{12}N_4O_2$ (MW=256.2 g/mol)

b) 7-Benzyl-1-methoxymethyl-3-methylxanthine 2.3 g (0.1 g atom) of sodium were dissolved in 200 ml of anhydrous methanol, treated with 25.6 g (0.1 mol) of xanthine from stage a), the mixture was heated under reflux until a clear solution was formed, then cooled and evaporated under reduced pressure and the residue was dried. The sodium salt of the 7-benzyl-3-methylxanthine thus obtained was suspended in 300 ml of anhydrous acetonitrile, a solution of 8.8 g (0.11 mol) of methoxymethyl chloride in 40 ml of acetonitrile was added dropwise with stirring at 50° C. and the mixture was additionally stirred at 50° C. for 8 hours. It was then cooled and evaporated under reduced pressure, the residue was taken up in chloroform, unreacted 7-benzyl-3-methylxanthine was extracted by shaking with 1 N sodium hydroxide solution, and the chloroform phase was washed with water until neutral, dried and evaporated under reduced pressure, 22 g (73.3% of theory) of oily product being obtained, which gradually solidified and could be recrystallized from ethyl acetate with addition of petroleum ether at boiling heat. $C_{15}H_{16}N_4O_3$ (MW=300.3 g/mol); melting point: 114° C. The introduction of the methoxymethyl group into the 1-position of the 7-benzyl-3-methylxanthine also takes place using methoxymethyl 4-toluenesulfonate as an alkylating agent, which is produced in a 1-pot reaction from 4-toluenesulfonyl chloride and sodium acetate or 4-toluenesulfonic acid and acetic anhydride with formaldehyde dimethyl acetal in dimethylformamide (WO 87/00523) and reacted in situ with 7-benzyl-3-methylxanthine.

c) 1-Methoxymethyl-3-methylxanthine (compound 1)

10.5 g (0.035 mol) of the 1,3,7-trisubstituted xanthine from stage b) were hydrogenated in 200 ml of glacial acetic acid over 1.5 g of palladium (10%) on active carbon at 60° C. and 3.5 bar in 48 hours. After cooling, the mixture was covered with a layer of nitrogen, the catalyst was filtered off, the filtrate was concentrated under reduced pressure and the solid residue was purified by filtration on a silica gel column in the eluent chloroform/methanol (10/1).

Yield:5.5 g (74.8% of theory); melting point: 218° C. $C_8H_{10}N_4O_3$ (MW=210.2 g/mol)

| Analysis: | calculated: | C | 45.71% | H | 4.80% | N | 26.66% |
|---|---|---|---|---|---|---|---|
| | found: | C | 45.98% | H | 4.86% | N | 26.98% |

Example 2

3-Cyclopropyl-1-(2-methoxyethyl)xanthine (compound 10)

a) 7-Benzyl-3-cyclopropylxanthine 10.4 g (0.26 mol) of sodium hydroxide dissolved in 110 ml of water were added to a suspension of 50 g (0.26 mol) of 3-cyclopropylxanthine in 300 ml of methanol and the reaction mixture was stirred for one hour at 70° C., then treated dropwise at the same temperature with 44.5 g (0.26 mol) of benzyl bromide and kept between 70° and 80° C. for 4 hours. 1.04 g (0.026 mol) of sodium hydroxide and 4.45 g (0.026 mol) of benzyl bromide were then added. After a further hour, the mixture was cooled and filtered cold on a suction filter and the product was washed with water on the suction filter. The crude product thus obtained could be employed without further purification.

Yield: 48 g (65.4% of theory); melting point: 204° C. $C_{15}H_{14}N_4O_2$ (MW=282.3 g/mol); mass spectrum: 283 (60%, M+H); 240 (21%); 91 (100%)

b) 7-Benzyl-3-cyclopropyl-1-(2-methoxyethyl) xanthine 2.2 g (15.9 mmol) of potassium carbonate were added to a hot solution of 3 g (11.0 mmol) of 7-benzyl-3-cyclopropylxanthine from stage a) in dimethylformamide at 60° C. and the mixture was stirred at 60° C. for one hour. 1.51 g (15.9 mmol) of 2-methoxyethyl chloride were then added dropwise and the mixture was stirred at 80° C. for 6 hours. It was then allowed to cool to room temperature and concentrated under reduced pressure. The oily residue was taken up in dichloromethane and extracted using 1 N sodium hydroxide solution, washed with water until neutral, dried over magnesium sulfate and concentrated under reduced pressure, and the residue was employed in stage c) without further purification.

Yield: 2.7 g (71.7% of theory); melting point: 117° C. $C_{18}H_{20}N_4O_3$ (MW=340.4 g/mol); mass spectrum: 340 (36%, M); 282 (43%); 148 (100%); 91 (86%)

c) 3-Cyclopropyl-1-(2-methoxyethyl)xanthine (compound 10)

2.2 g (6.45 mmol) of the 1,3,7-trisubstituted xanthine from stage b) were hydrogenated in 250 ml of ethanol over 1.05 g of palladium (10%) on active carbon in 12 hours. The mixture was covered with a layer of nitrogen, the catalyst was filtered off, the filtrate was concentrated under reduced pressure and the residue was purified by flash chromatography on a silica gel column, toluene/ethanol (10/1).

Yield: 0.77 g (47.7% of theory); melting point: 203° C. $C_{11}H_{14}N_4O_3$ (MW=250.3 g/mol); mass spectrum: 250 (55%, M); 192 (100%); 149 (56%); 148 (58%); 121 (82%); 120 (56%)

Example 3

3-Butyl-1-(3-methoxypropyl)xanthine (compound 14)

a) 7-Benzyl-3-butylxanthine 10 g (0.25 mol) of sodium hydroxide dissolved in 100 ml of water were added to a suspension of 52 g (0.25 mol) of 3-butylxanthine in 300 ml of methanol and the reaction mixture was stirred at 70° C. for one hour, then treated dropwise at the same temperature with 42.8 g (0.25 mol) of benzyl bromide and kept between 70° and 80° C. for 5 hours. 1.0 g (0.025 mol) of sodium hydroxide and 4.28 g (0.025 mol) of benzyl bromide were then added. After a further 2 hours, the mixture was cooled, diluted with 1500 ml of water and filtered cold on a suction filter, the product was washed with water on the suction filter and dissolved in 1000 ml of 1 N sodium hydroxide solution, and the solution was filtered and slowly brought to pH 3 with stirring using concentrated hydrochloric acid. The crystallizate was filtered off from the solution, washed with water until chloride-free and dried under reduced pressure.

Yield: 54.1 g (72.5% of theory); melting point: 187° C.
$C_{16}H_{18}N_4O_2$ (MW=298.3 g/mol); mass spectrum: 298 (13%, M); 91 (100%)

b) 7-Benzyl-3-butyl-1-(3-methoxypropyl)xanthine 2.1 g (15.2 mmol) of potassium carbonate were added to a hot solution of 3 g (10.0 mmol) of 7-benzyl-3-butylxanthine from stage a) in 90 ml of dimethylformamide at 60° C. and the mixture was stirred at 60° C. for one hour. 1.3 g (12.0 mol) of 3-methoxypropyl chloride were then added dropwise and the mixture was stirred at 100° C. for 3 hours. It was then allowed to cool to room temperature, and was treated with water and extracted using dichloromethane. The organic phase was washed with water and 1 N sodium hydroxide solution, dried using sodium sulfate and concentrated under reduced pressure. The oily residue was purified by flash chromatography on a silica gel column, toluene/ethanol (39/1)

Yield: 3.2g (86.5% of theory); yellow oil
$C_{20}H_{26}N_4O_3$ (MW=370.5 g/mol); mass spectrum: 371.3 (100%, M+H); 339.3 (16%); 298.3 (15%); $^1$H-NMR (DMSO-d$_6$, 200 MHz): δ=0.90 (t, 3 H, CH$_2$C$\underline{H}_3$); 1.30 (sext., 2 H, C$\underline{H}_2$CH$_2$CH$_3$); 1.63 and 1.75 (2 quint., 4 H, CH$_2$C$\underline{H}_2$CH$_2$); 3.32 (s, 3 H, OCH$_3$); 3.34 (t, 2 H, OC$\underline{H}_2$); 5.48 (s, 2 H, benz. H); 7.25–7.40 (m, 5 H, aromat. H); 8.26 (s, 1 H, N=C$\underline{H}$)

c) 3-Butyl-1-(3-methoxypropyl)xanthine (compound 14)

0.5 g (1.35 mmol) of the 1,3,7-trisubstituted xanthine from stage b) were hydrogenated in 50 ml of ethanol over 0.1 g of palladium (10%) on active carbon in 5 hours. The mixture was covered with a layer of nitrogen, the catalyst was filtered off and the filtrate was concentrated under reduced pressure. The residue could be recrystallized from methanol/methyl tert-butyl ether.

Yield: 0.19 g (52.2% of theory); melting point: 157° C.
$C_{13}H_{20}N_4O_3$ (MW=280.3 g/mol); mass spectrum: 281.3 (M+H, 100%); 249.2 (M—OMe, 70%)

Example 4

1-Ethoxymethyl-3-propylxanthine (compound 18)

a) 7-Benzyl-3-propylxanthine 4.12 g (0.103 mol) of sodium hydroxide dissolved in 41 ml of water were added to a suspension of 20 g (0.103 mol) of 3-propylxanthine in 112 ml of methanol and the reaction mixture was stirred at 70° C. for one hour, then treated dropwise at the same temperature with 12.23 ml (0.103 mol) of benzyl bromide and kept between 70° and 80° C. for 4 hours. The mixture was cooled, filtered cold on a suction filter, and the product was washed with water on the suction filter and dried under reduced pressure.

Yield: 20.3 g (69.4% of theory); melting point: 186° C.
$C_{15}H_{16}N_4O_2$ (MW=284.3 g/mol); mass spectrum: 284 (18%, M); 242 (11%); 212 (13%); 91 (100%)

b) 7-Benzyl-1-ethoxymethyl-3-propylxanthine 1.71 g (12.0 mmol) of potassium carbonate were added to a hot solution of 2.2 g (7.7 mmol) of 7-benzyl-3-propylxanthine from stage a) in 60 ml of dimethylformamide at 60° C. and the mixture was stirred at 60° C. for 1 hour. 0.93 ml (10.0 mmol) of ethoxymethyl chloride was then added dropwise and the mixture was stirred at 80° C. for 4.5 hours. A further 0.5 ml (5.3 mmol) of ethoxymethyl chloride was then added and the mixture was again stirred for 6 hours. 12 ml of water and 5 ml of methanol were then added, the mixture was allowed to stand overnight, 60 ml of water were added again and the mixture was extracted three times using methyl tert-butyl ether. The combined organic phases were washed twice with water, dried using magnesium sulfate and concentrated under reduced pressure. The crude product was purified by flash chromatography on a silica gel column, dichloromethane/methanol (19.8/0.2).

Yield: 2.28 g (87% of theory); melting point: 110° C.
$C_{18}H_{22}N_4O_3$ (MW=342.4 g/mol); mass spectrum:342 (7%, M); 296 (13%); 285 (33%); 91 (100%)

c) 1-Ethoxymethyl-3-propylxanthine (compound 18)

1.79 g (5.2 mmol) of the 1,3,7-trisubstituted xanthine from stage b) were hydrogenated in 200 ml of ethanol over 179 mg of palladium (10%) on active carbon in 6.5 hours. The mixture was covered with a layer of nitrogen, the catalyst was filtered off and the filtrate was concentrated under reduced pressure. The residue was purified by flash chromatography on a silica gel column, dichloromethane/methanol (19.8/0.2).

Yield: 1.12 g (85% of theory); melting point: 134° C.
$C_{11}H_{16}N_4O_3$ (MW=252.3 g/mol); mass spectrum: 252 (29%, M); 208 (40%); 195 (100%); 166 (65%); 136 (50%)

Example 5

3-Ethyl-1-propoxymethylxanthine (compound 27)

a) 7-Benzyl-3-ethylxanthine 180 g (1 mol) of 3-ethylxanthine were initially introduced into 1000 ml of dimethylformamide, the mixture was heated to 80° C. with stirring and, after the introduction of 88 g (0.64 mol) of potassium carbonate, treated dropwise with 133 g (1.05 mol) of benzyl chloride in the course of 1 hour. It was then stirred at 100° C. for 2 hours, treated with 1000 ml of water, and the precipitated product was filtered on a suction filter, washed with water until salt-free and dried in a vacuum drying oven at 100° C. If necessary, a further purification can be carried out by reprecipitating from 1 N sodium hydroxide solution using 4 N hydrochloric acid analogously to Example 1a).

Yield: 262 g (97% of theory) melting point: 218° C.
$C_{14}H_{14}N_4O_2$ (MW=270.3 g/mol)

| Analysis: | calculated: | C | 62.21% | H | 5.22% | N | 20.73% |
|---|---|---|---|---|---|---|---|
| | found: | C | 62.07% | H | 5.36% | N | 20.84% | b) 7-Benzyl-3-ethyl-1-propoxymethylxanthine

Analogously to Example 1b), 27 g (0.1 mol) of 7-benzyl-3-ethylxanthine were converted into the sodium salt, then reacted in acetonitrile with 13 g (0.12 mol) of propoxymethyl chloride (prepared in 67% yield from 1,3,5-trioxane, 1-propanol and hydrogen chloride gas) and worked up, 30 g (87.6% of theory) of analytically pure product being obtained, which could optionally be recrystallized from ethyl acetate. $C_{18}H_{22}N_4O_3$ (MW=342.4 g/mol); melting point: 92° C.

| Analysis: | calculated: | C | 63.14% | H | 6.48% | N | 16.36% |
|---|---|---|---|---|---|---|---|
| | found: | C | 62.95% | H | 6.55% | N | 16.21% | c) 3-Ethyl-1-propoxymethylxanthine (compound 27)

7.1 g (0.05 mol) of the product from stage b) and 5 g (0.08 mol) of ammonium formate were stirred for several days over 6 g of palladium (10%) on active carbon at 35° C. in 150 ml of ethanol, a successive addition of further ammonium formate up to a total amount of 22 g (0.35 mol) proving appropriate. The mixture was filtered, the filtrate was concentrated, the residue was taken up in sodium carbonate solution, the solution was washed with chloroform, the aqueous phase was brought to pH 4 using 2 N hydrochloric acid, the product was extracted by shaking with chloroform and, after drying and evaporating, the residue was recrystallized from ethyl acetate.

Yield: 8.6 g (68.2% of theory); melting point: 159° C.
$C_{11}H_{16}N_4O_3$ (MW=252.3 g/mol)

| Analysis: | calculated: | C | 52.37% | H | 6.39% | N | 22.21% |
|---|---|---|---|---|---|---|---|
| | found : | C | 52.85% | H | 6.88% | N | 22.50% |

Hydrogenolytic debenzylation analogously to Example 1 c) yielded the same compound in 58.9% yield.

Example 6

3-Isobutyl-1-propoxymethylxanthine (compound 31)

a) 7-Benzylguanine hydrochloride 40 ml (0.34 ml) of benzyl bromide were added dropwise to a suspension of 40 g (0.147 mol) of guanosine in 200 ml of dimethyl sulfoxide and the mixture was stirred at room temperature for 4 hours. It was treated with 100 ml of concentrated hydrochloric acid and stirred at room temperature for 30 minutes. It was then poured into 1200 ml of methanol, and the precipitate was filtered off with suction and washed with methanol.

Yield: 35.9 g (92% of theory); melting point:>325° C.
$C_{12}H_{12}ClN_5O$ (MW=277.7 g/mol); base: $C_{12}H_{11}N_5O$ (MW=241.6 g/mol) mass spectrum: 242.2 (100%, M+H)

b) 7-Benzylxanthine 35.9 g (0.13 mol) of 7-benzylguanine hydrochloride from stage a) were dissolved in a mixture of 90 ml of water and 807 ml of glacial acetic acid and heated to 100° C. After cooling to 50° C., a solution of 35.88 g (0.52 mol) of sodium nitrite in 90 ml of water was added in one portion. After 16 hours at room temperature, the resulting precipitate was filtered off with suction, washed with water on the suction filter and dried.

Yield: 26.0 g (83% of theory); melting point:>266° C.
$C_{12}H_{10}N_4O_2$ (MW=242.5 g/mol); mass spectrum: 243.1 (95%, M+H); 91 (100%)

c) 7-Benzyl-3-isobutylxanthine 1.5 g (6.2 mmol) of 7-benzylxanthine from stage b) were dissolved in 50 ml of dimethylformamide at 50° C. and treated in portions with 0.149 g (6.2 mmol) of sodium hydride and stirred at 50° C. for one hour. 0.67 ml (6.2 mmol) of isobutyl bromide was added dropwise and the mixture was heated to 80° C. After 5 hours, a further 0.2 ml (1.86 mmol) of isobutyl bromide was added and the mixture was stirred for a further 5 hours. 12 ml of water and 5 ml of methanol were then added, the mixture was stirred at room temperature for 2 hours, a further 60 ml of water were added and the mixture was extracted three times using methyl tert-butyl ether. The organic phases were washed with water, dried using magnesium sulfate and concentrated under reduced pressure and the residue was purified by flash chromatography on a silica gel column, dichloromethane/methanol (99/1).

Yield: 1.16 g (63% of theory); $C_{16}H_{18}N_4O_2$ (MW=298.3 g/mol)

$^1$H-NMR (DMSO-$d_6$, 200 MHz): δ=0.85 (d, 6 H, CH(C$\underline{H}_3$)$_2$); 2.16 (m, 1 H, CH$_2$C$\underline{H}$(CH$_3$)$_2$); 3.73 (d, 2H, C$\underline{H}_2$CH); 5.45 (s, 2H, benzyl. H); 7.23–7.40 (m, 5 H, aromat. H), 8.20 (s, 1 H, N=C$\underline{H}$); 11.13 (s br., 1 H, N$\underline{H}$)

d) 7-Benzyl-3-isobutyl-1-propoxymethylxanthine 0.86 g (6.2 mmol) of potassium carbonate was added at 60° C. to a suspension of 1.16 g (3.9 mmol) of 7-benzyl-3-isobutylxanthine from stage c) in 60 ml of dimethylformamide and the mixture was stirred at this temperature for 1 hour. 0.56 ml (5.1 mmol) of propoxymethyl chloride was then added dropwise and the mixture was stirred at 80° C. for 5.5 hours. 12 ml of water and 5 ml of methanol were then added, the mixture was allowed to stand overnight, 60 ml of water were again added and the mixture was extracted four times using 150 ml of methyl tert-butyl ether each time. The combined organic phases were washed with 200 ml of water, dried using magnesium sulfate and concentrated under reduced pressure. The crude product was purified by flash chromatography on a silica gel column, dichloromethane.

Yield: 1.2 g (83% of theory); melting point: 72° C.
$C_{20}H_{26}N_4O_3$ (MW=370.5 g/mol); mass spectrum: 370 (40%, M); 310 (55%); 299 (100%); 256 (55%); 91 (85%)

e) 3-Isobutyl-1-propoxymethylxanthine (compound 31)

859 mg (2.32 mmol) of the 1,3,7-trisubstituted xanthine from stage d) were hydrogenated in 22 ml of ethanol over 86 mg of palladium (10%) on active carbon in 6 hours. The mixture was covered with a layer of nitrogen, the catalyst was filtered off and the filtrate was concentrated under reduced pressure. The residue was purified by flash chromatography on a silica gel column, dichloromethane/methanol (19/1).

Yield: 588 mg (90% of theory); melting point: 141° C.
$C_{13}H_{20}N_4O_3$ (MW=280.3 g/mol); mass spectrum: 280 (25%, M); 222 (37%); 209 (100%); 166 (85%); 136 (55%)

Example 7

3-Phenyl-1-propoxymethylxanthine (compound 32)

a) 7-Benzyl-3-phenylxanthine

A solution of 0.53 g (13.2 mmol) of sodium hydroxide in 5.3 ml of water was added to a suspension of 3.0 g (13.2 mmol) of 3-phenylxanthine in 18 ml of methanol and the mixture was stirred at 70° C. for 1 hour. It was then treated dropwise with 1.56 ml (13.2 mmol) of benzyl bromide and stirred at 70° C. for 7 hours, the precipitate was filtered off with suction after cooling, washed with water and dissolved in 50 ml of 1 N sodium hydroxide solution, insoluble matter was filtered off and the solution was adjusted to pH 8–9 using 4 N hydrochloric acid. The resulting precipitate was filtered off with suction, washed with water and purified by flash chromatography on a silica gel column, dichloromethane/methanol (79/1).

Yield: 1.13 g (27% of theory); melting point: 250° C.

$C_{18}H_{14}N_4O_2$ (MW=318.6 g/mol); mass spectrum: 319 (100%, M+H); 91 (19%)

b) 7-Benzyl-3-phenyl-1-propoxymethylxanthine 0.45 g (3.26 mmol) of potassium carbonate was added at 60° C. to a suspension of 0.65 g (2.04 mmol) of 7-benzyl-3-phenylxanthine from stage a) in 20 ml of dimethylformamide and the mixture was stirred at this temperature for one hour. 0.29 ml (2.65 mmol) of propoxymethyl chloride was then added dropwise and the mixture was stirred at 80° C. for 1.5 hours. 20 ml of water were then added, the mixture was extracted three times using 24 ml of methyl tert-butyl ether each time, and the combined organic phases were washed twice with 12 ml of water each time, dried using magnesium sulfate and concentrated under reduced pressure. The crude product was purified by flash chromatography on a silica gel column heptane/ethyl acetate (5/7).

Yield: 0.69 g (87% of theory), melting point: 103° C.

$C_{22}H_{22}N_4O_3$ (MW=390.4 g/mol); mass spectrum: 391.2 (100%, M+H); 331.2 (12%); 241.1 (25%)

c) 3-Phenyl-1-propoxymethylxanthine (compound 32)

535 mg (1.37 mmol) of the 1,3,7-trisubstituted xanthine from stage b) were hydrogenated in 20 ml of ethanol over 50 mg of palladium (10%) on active carbon. The mixture was covered with a layer of nitrogen, the catalyst was filtered off and the filtrate was concentrated under reduced pressure. The residue was purified by flash chromatography on a silica gel column, dichloromethane/methanol (19/0.3).

Yield: 232 mg (56% of theory); melting point: 220° C.

$C_{15}H_{16}N_4O_3$ (MW=300.3 g/mol); mass spectrum:300 (23%, M); 242 (68%); 229 (55%); 185 (100%)

Example 8

3-Cyclopropylmethyl-1-propoxymethylxanthine (compound 34)

a) 7-Benzyl-3-cyclopropylmethylxanthine

A solution of 7 g (29.0 mmol) of 7-benzylxanthine from Example 6 b) in 200 ml of dimethylformamide was heated to 50° C. and treated in portions with 0.69 g (29.0) mmol of sodium hydride and stirred at 50° C. for one hour. 2.76 ml (29.0 mmol) of cyclopropylmethyl bromide were added to this suspension and the temperature was increased to 80° C. After 7 hours at 80° C., 1 ml (11.0 mmol) of cyclopropylmethyl bromide was added again. After a further 6 hours, 24 ml of water and 10 ml of methanol were added, and the mixture was allowed to stand overnight, treated again with 120 ml of water and extracted three times using 300 ml of methyl tert-butyl ether each time. The organic phases were washed with water, dried using magnesium sulfate and concentrated under reduced pressure. The crude product was purified by flash chromatography on a silica gel column, dichloromethane/methanol (99/1).

Yield: 4.8 g (56% of theory); melting point: 185° C.

$C_{16}H_{16}N_4O_2$ (MW=296.4 g/mol); mass spectrum: 297.3 (100%, M+H)

b) 7-Benzyl-3-cyclopropylmethyl-1-propoxymethylxanthine 1.12 g (8.1 mmol) of potassium carbonate were added at 60° C. to a solution of 1.5 g (5.06 mmol) of 7-benzyl-3-cyclopropylmethylxanthine from stage a) in 60 ml of dimethylformamide and the mixture was stirred at this temperature for one hour. 722 µl (6.58 mmol) of propoxymethyl chloride were then added dropwise and the mixture was stirred at 80° C. for 4 hours. 12 ml of water and 5 ml of methanol were added and the mixture was stirred at 50° C. for 2 hours. 60 ml of water were then added again, the mixture was extracted three times using methyl tert-butyl ether, and the combined organic phases were washed twice with water, dried using magnesium sulfate and concentrated under reduced pressure. The crude product was purified by flash chromatography on a silica gel column, dichloromethane/methanol (19.8/0.2).

Yield: 1.32 g (71% of theory); melting point: 88° C.;

$C_{20}H_{24}N_4O_3$ (MW=368.4 g/mol); mass spectrum: 368 (9%, M); 310 (11%); 297 (13%); 91 (100%)

c) 3-Cyclopropylmethyl-1-propoxymethylxanthine (compound 34)

938 mg (2.55 mmol) of the 1,3,7-trisubstituted xanthine from stage b) were hydrogenated in 60 ml of ethanol over 130 mg of palladium (10%) on active carbon in 15 hours. The mixture was covered with a layer of nitrogen, the catalyst was filtered off and the filtrate was concentrated under reduced pressure. The residue was purified by flash chromatography on a silica gel column, dichloromethane/methanol (39/1).

Yield: 671 mg (95% of theory); melting point: 132° C.

$C_{13}H_{18}N_4O_3$ (MW=278.3 g/mol); mass spectrum: 278 (26%, M); 220 (80%); 207 (64%); 136 (87%); 122 (67%); 55 (100%)

Example 9

1-(2-Propoxyethyl)-3-propylxanthine (compound 37)

a) 7-Benzyl-1-(2-propoxyethyl)-3-propylxanthine 1.7 g (12.48 mmol) of potassium carbonate were added at 60° C. to a suspension of 2.2 g (7.8 mmol) of 7-benzyl-3-propylxanthine (prepared according to Example 4a) in 70 ml of dimethylformamide and the mixture was stirred at this temperature for one hour. 1.3 ml (10.14 mmol) of 2-propoxyethyl chloride were then added dropwise and the mixture was stirred at 80° C. for 10 hours. 1.2 ml of methanol and 14 ml of water were then added, and the mixture was allowed to stand overnight, treated with a further 70 ml of water and extracted three times using 84 ml of methyl tert-butyl ether each time. The combined organic phases were washed twice with 42 ml of water each time, dried using magnesium sulfate and concentrated under reduced pressure. The crude product was purified by flash chromatography on a silica gel column, dichloromethae/methanol (19/0.1).

Yield: 2.3 g (80% of theory); melting point: 55° C.

$C_{19}H_{24}N_4O_3$ (MW=356.4 g/mol); mass spectrum: 356 (10%, M); 297 (15%); 285 (38%); 91 (100%)

b) 1-(2-Propoxyethyl)-3-propylxanthine (compound 37)

1.75 g (4.7 mmol) of the 1,3,7-trisubstituted xanthine from stage a) were hydrogenated in 75 ml of ethanol over 0.2 g of palladium (10%) on active carbon in 6 hours. The mixture was covered with a layer of nitrogen, the catalyst was filtered off and the filtrate was concentrated under reduced pressure. The residue was purified by flash chromatography on a silica gel column, dichloromethane/methanol (38/1).

Yield: 0.93 g (70% of theory); melting point: 137° C.; $C_{13}H_{20}N_4O_3$ (MW=280.6 g/mol); mass spectrum: 281.3 (45%, M+H); 221.2 (100%)

Example 10

1 Butoxymethyl-3-isopropylxanthine (compound 42)

a) 7-Benzyl-3-isopropylxanthine

A solution of 3.5 g (1.45 mmol) of 7-benzylxanthine from Example 6b) in 60 ml of dimethylformamide was heated to 50° C. and treated in portions with 0.35 g (1.45 mmol) of sodium hydride, diluted with 20 ml of dimethylformamide and stirred at 50° C. for one hour. 1.36 ml (1.45 mmol) of 2-bromopropane were added to this suspension and the temperature was increased to 80° C. In the course of the reaction, a total of 4.91 ml (52.3 mmol) of 2-bromopropane were additionally added. After a total of 16 hours at 80° C., 10 ml of water and 2 ml of methanol were added, and the mixture was stirred for 10 minutes, treated with a further 70 ml of water and extracted three times using 70 ml of methyl tert-butyl ether. The organic phases were washed with water, dried using magnesium sulfate and concentrated under reduced pressure. The crude product was purified by flash chromatography on a silica gel column, dichloromethane/methanol (19/0.4).

Yield: 1.17 g (29% of theory); melting point: 219° C. $C_{15}H_{18}N_4O_2$ (MW=286.6 g/mol); mass spectrum: 285.2 (100%, M+H)

b) 7-Benzyl-1-butoxymethyl-3-isopropylxanthine 0.583 g (4.22 mmol) of potassium carbonate was added at 60° C. to a suspension of 0.75 g (2.64 mmol) of 7-benzyl-3-isopropylxanthine from stage a) in 20 ml of dimethylformamide and the mixture was stirred at this temperature for one hour. 0.42 g (3.43 mmol) of butoxymethyl chloride was then added dropwise and the mixture was stirred at 80° C. for 6 hours. A further 0.11 g (0.87 mmol) of butoxymethyl chloride was then added and the mixture was stirred again for 5 hours. 20 ml of water were then added, the mixture was extracted three times using 30 ml of methyl tert-butyl ether each time, and the combined organic phases were washed twice with 20 ml of water each time, dried using magnesium sulfate and concentrated under reduced pressure. The crude product was purified by flash chromatography on a silica gel column, heptane/ethyl acetate (2/1).

Yield: 0.66 g (68% of theory); oil; $C_{20}H_{26}N_4O_2$ (MW=370.7 g/mol) mass spectrum: 371.4 (100%, M+H); 297.2 (33%);

$^1$H-NMR (DMSO-$d_6$, 200 MHz): δ=0.82 (t, 3 H ($CH_2$)$_3$C$\underline{H}_3$); 1.48 (d, 6 H, CH(C$\underline{H}_3$)$_2$); 1.14–1.56 (m, 4 H, $CH_2$(C$\underline{H}_2$)$_2$CH$_3$); 3.50 (t, 2 H, OC$\underline{H}_2$); 5.06 (m, 1 H, C$\underline{H}$(CH$_3$)$_2$); 5.30 (s, 2H, benzyl. H); 5.50 (s, 2 H, OC$\underline{H}_2$N); 7.24–7.43 (m, 5 H, aromat. H); 8.31 (s, 1 H, N=C$\underline{H}$)

c) 1-Butoxymethyl-3-isopropylxanthine (compound 42)

660 mg (1.78 mmol) of the 1,3,7-trisubstituted xanthine from stage b) were hydrogenated in 60 ml of ethanol over 86 mg of palladium (10%) on active carbon in 14 hours. The mixture was covered with a layer of nitrogen, the catalyst was filtered off and the filtrate was concentrated under reduced pressure. The residue was purified by flash chromatography on a silica gel column, dichloromethane/methanol (19/0.3).

Yield: 416 mg (83% of theory); melting point: 131° C. $C_{13}H_{20}N_4O_3$ (MW=280.3 g/mol); mass spectrum: 281.2 (100%, M+H); 207.2 (30%)

Example 11

1-Isobutoxymethyl-3-methylxanthine (compound 48)

a) 7-Benzyl-1-isobutoxymethyl-3-methylxanthine 1.9 g (14.08 mmol) of potassium carbonate were added at 60° C. to a suspension of 2.25 g (8.8 mmol) of 7-benzyl-3-methylxanthine (prepared according to Example 1 a) in 50 ml of N-methylpyrrolidone and the mixture was stirred at this temperature for one hour. 1.4 g (11.44 mmol) of isobutoxymethyl chloride were then added dropwise and the mixture was stirred at 80° C. for 3 hours. A further 0.5 g (4.4 mmol) of isobutoxymethyl chloride was then added and the mixture was stirred again for 2 hours. 50 ml of water were then added and the mixture was extracted three times using 60 ml of methyl tert-butyl ether each time. The combined organic phases were washed twice with 30 ml of water each time, dried using magnesium sulfate and concentrated under reduced pressure. The crude product was purified by flash chromatography on a silica gel column, dichloromethane/methanol (19/0.2).

Yield: 2.54 g (85% of theory); melting point: 76° C. $C_{18}H_{22}N_4O_3$ (MW=342.4 g/mol); mass spectrum: 343.3 (100%, M+H); 269.2 (88%); 179.1 (24%)

b) 1-Isobutoxymethyl-3-methylxanthine (compound 48)

2.1 g (6.14 mmol) of the 1,3,7-trisubstituted xanthine from stage a) were hydrogenated in 50 ml of ethanol over 0.4 g of palladium (10%) on active carbon in 25 hours. The mixture was covered with a layer of nitrogen, the catalyst was filtered off and the filtrate was concentrated under reduced pressure. The residue was purified by flash chromatography on a silica gel column, dichloromethane/methanol (19/0.3).

Yield: 0.59 g (38% of theory); melting point: 160° C. $C_{11}H_{16}N_4O_3$ (MW=252.3 g/mol); mass spectrum: 252 (7%, M); 196 (10%); 180 (100%); 179 (88%); 167 (56%)

Example 12

1-sec-Butoxymethyl-3-ethylxanthine (compound 52)

a) 7-Benzyl-1-sec-butoxymethyl-3-ethylxanthine 2.45 g (18.0 mmol) of potassium carbonate were added at 60° C. to a suspension of 3.0 g (11.0 mmol) of 7-benzyl-3-ethylxanthine (prepared according to Example 5a) in 60 ml of dimethylformamide and the mixture was stirred at this temperature for one hour. 1.77 g (14.0 mmol) of sec-butoxymethyl chloride were then added dropwise and the mixture was stirred at 80° C. for 5 hours. 0.7 g (5.5 mmol) of sec-butoxymethyl chloride was then added again and the mixture was stirred for a further 3 hours. 12 ml of water and 5 ml of methanol were then added and the mixture was stirred at 50° C. for 2 hours. A further 60 ml of water were then added, the mixture was extracted three times using 200 ml of methyl tert-butyl ether each time, and the combined organic phases were washed with 200 ml of water, dried using magnesium sulfate and concentrated under reduced pressure. The crude product was purified by flash chromatography on a silica gel column, dichloromethane/methanol (19.8/0.2).

Yield: 3.29 g (84% of theory); oil; $C_{19}H_{24}N_4O_3$ (MW= 356.4 g/mol) mass spectrum: 356 (4%, M); 284 (71%); 271 (32%); 91 (100%);

$^1$H-NMR (DMSO-$d_6$, 200 MHz): δ=0.73 (t, 3 H CH$_2$C$\underline{H}_3$); 1.05 (d, 3 H, CHC$\underline{H}_3$); 1.21 (t, 3 H, NCH$_2$C$\underline{H}_3$); 1.35 (quint., 2 H, CHC$\underline{H}_2$CH$_3$); 3.57 (sext., 1 H, C$\underline{H}$CH$_2$); 4.02 (q, 2 H, NC$\underline{H}_2$CH$_3$); 5.30 (AB system, 2 H, OC$\underline{H}_2$N); 5.50 (s, 2 H, benzyl. H); 7.23–7.40 (m, 5 H, aromat. H); 8.32 (s, 1 H, N=C$\underline{H}$)

b) 1-sec-Butoxymethyl-3-ethylxanthine (compound 52)

2.73 g (7.66 mmol) of the 1,3,7-trisubstituted xanthine from stage a) were hydrogenated in 100 ml of ethanol over 273 mg of palladium (10%) on active carbon in 12.5 hours. The mixture was covered with a layer of nitrogen, the catalyst was filtered off and the filtrate was concentrated under reduced pressure. The residue was purified by flash chromatography on a silica gel column, dichloromethane/methanol (19.7/0.3).

Yield: 1.82 g (89% of theory); melting point: 189° C.

$C_{12}H_{18}N_4O_3$ (MW=266.3 g/mol); mass spectrum: 266 (4%, M); 194 (87%); 193 (100%); 181 (63%); 136 (87%)

Example 13

1-(2-Methoxyethoxymethyl)-3-methylxanthine (compound 53)

a) 7-Benzyl-1-(2-methoxyethoxymethyl)-3-methylxanthine

The mixture of 25.6 g (0.1 mol) of 7-benzyl-3-methylxanthine (prepared according to Example 1a), 15.2 g (0.11 mol) of potassium carbonate and 16.2 g (0.13 mol) of 2-methoxyethoxymethyl chloride in 500 ml of acetonitrile was heated at 50° C. with stirring for 5 hours, then worked up analogously to Example 1b) and the oily product obtained was purified by means of filtration on a silica gel column in the eluent chloroform/methanol (10/1).

Yield: 22.8 g (66.2% of theory); oil; $C_{17}H_{20}N_4O_4$ (MW= 344.3 g/mol)

| Analysis: | calculated: | C | 59.29% | H | 5.85% | N | 16.27% |
|---|---|---|---|---|---|---|---|
| | found: | C | 59.01% | H | 5.93% | N | 16.02% | b) 1-(2-Methoxyethoxymethyl)-3-methylxanthine (compound 53)

The hydrogenolytic debenzylation of 22.7 g (0.066 mol) of the compound from stage a) according to Example 1c) yielded, after chromatographic purification and recrystallization from ethanol, 10.9 g of final product (65% of theory).

$C_{10}H_{14}N_4O_4$ (MW=254.3 g/mol); melting point: 188° C.

| Analysis: | calculated: | C | 47.24% | H | 5.55% | N | 22.04% |
|---|---|---|---|---|---|---|---|
| | found: | C | 47.22% | H | 5.45% | N | 22.06% |

Example 14

3-Ethyl-1-(2-(2-methoxyethoxy)ethyl)xanthine (compound 56)

14 g (0.037 mol) of 7-benzyl-3-ethyl-1-(2-(2-methoxyethoxy)ethyl)xanthine were prepared from 7-benzyl-3-ethylxanthine (prepared according to Example 5a) and 1-bromo-2-(2-methoxyethoxy)ethane (prepared according to Example 2b) in a yield of 98% of theory ($C_{19}H_{24}N_4O_4$ (MW=372.4 g/mol); melting point after recrystallization from diisopropyl ether: 64° C.

Analysis: calculated: C 61.28% H 6.50% N 15.04% found: C 61.44% H 6.49% N 15.26%) and hydrogenolytically debenzylated analogously to Example 1c). The crude product obtained was recrystallized directly from ethyl acetate without purification by column chromatography. Yield: 7.5 g (71.8% of theory); melting point: 140° C.; $C_{12}H_{18}N_4O_4$ (MW=282.3 g/mol)

| Analysis: | calculated: | C | 51.05% | H | 6.43% | N | 19.85% |
|---|---|---|---|---|---|---|---|
| | found: | C | 51.51% | H | 6.37% | N | 19.87% |

Example 15

3-Methyl-1-(2-phenoxyethyl)xanthine (compound 60)

a) 7-Benzyl-3-methyl-1-(2-phenoxyethyl)xanthine 2.6 g (18.72 mmol) of potassium carbonate were added at 60° C. to a suspension of 3.0 g (11.7 mmol) of 7-benzyl-3-methylxanthine (prepared according to Example 1a) in 70 ml of dimethylformamide and the mixture was stirred at this temperature for one hour. 3.1 g (15.21 mmol) of 2-phenoxyethyl bromide were then added dropwise and the mixture was stirred at 80° C. for 5 hours. The crude mixture was then filtered, the filtrate was concentrated under reduced pressure, the residue was taken up in dichloromethane and the solution was washed once with 1 N sodium hydroxide solution and twice with water. The organic phases were dried using magnesium sulfate and concentrated under reduced pressure. The crude product was purified by flash chromatography on a silica gel column, heptane/ethyl acetate (1/2).

Yield: 3.52 g (80% of theory); melting point: 141° C.; $C_{21}H_{20}N_4O_3$ (MW=376.4 g/mol); mass spectrum: 376 (2%, M); 283 (100%); 91 (87%)

b) 3-Methyl-1-(2-phenoxyethyl)xanthine (compound 60)

3.0 g (8.0 mmol) of the 1,3,7-trisubstituted xanthine from stage a) were hydrogenated in 500 ml of ethanol over 0.3 g of palladium (10%) on active carbon in 6 hours. The mixture was covered with a layer of nitrogen, the catalyst was filtered off and the filtrate was concentrated under reduced pressure. The residue was purified by flash chromatography on a silica gel column, heptane/ethyl acetate (1/10).

Yield: 1.09 g (48% of theory); melting point: 207° C.; $C_{14}H_{14}N_4O_3$ (MW=286.3 g/mol); mass spectrum: 287.2 (45%, M+H); 193.1 (100%)

Example 16

1-(4-Chlorophenoxymethyl)-3-methylxanthine (compound 65)

a) 7-Benzyl-1-(4-chlorophenoxymethyl)-3-methylxanthine 2.59 g (19.0 mmol) of potassium carbonate were added at 60° C. to a suspension of 3.0 g (12.0 mmol) of 7-benzyl-3-methylxanthine (prepared according to Example 1a) in 50 ml of dimethylformamide and the mixture was stirred at this temperature for one hour. 2.69 g (15.0 mmol) of 4-chlorophenoxymethyl chloride were then added dropwise and the mixture was stirred at 80° C. for 8 hours. The crude mixture was then filtered, the filtrate was concentrated under reduced pressure, the residue was taken up in dichloromethane, and the solution was washed once with 1 N sodium hydroxide solution and twice with water. The organic phases were dried using magnesium sulfate and concentrated under reduced pressure. The crude product was purified by flash chromatography on a silica gel column, dichloromethane/methanol (19.8/0.2) Yield: 4.15 g (87% of theory); melting point: 96° C.

$C_{20}H_{17}ClN_4O_3$ (MW=396.8 g/mol); mass spectrum: 398 (2%, $^{37}Cl$, M); 396 (6%, $^{35}Cl$, M); 269 (100%); 91 (72%)

b) 1-(4-Chlorophenoxymethyl)-3-methylxanthine (compound 65)

3.37 g (8.5 mmol) of the 1,3,7-trisubstituted xanthine from stage a) were hydrogenated in 450 ml of ethanol over 0.34 g of palladium (10%) on active carbon in 5 hours. The mixture was covered with a layer of nitrogen, the catalyst was filtered off and the filtrate was concentrated under reduced pressure. The residue was purified by flash chromatography on an RP-18 column, water/acetonitrile (7/3).

Yield: 0.91 g (34% of theory); melting point: 218° C.

$C_{13}H_{11}ClN_4O_3$ (MW=306.7 g/mol); mass spectrum: 309.1 (6%, $^{37}Cl$, M+H); 307.1 (19%, $^{35}Cl$, M+H); 179.1 (100%); 167.1 (11%)

Example 17

1-Benzyloxymethyl-3-methylxanthine (compound 68)

a) 3-Methyl-7-tritylxanthine 0.62 g (25.88 mmol) of sodium hydride was added in portions at 60° C. to a suspension of 3.9 g (23.5 mmol) of 3-methylxanthine in 85 ml of dimethylformamide, and the mixture was stirred at this temperature for 1.5 hours and heated to 90° C. 6.6 g (23.67 mmol) of trityl chloride in 30 ml of dimethylformamide were then added and the mixture was stirred at 90° C. for 3 hours. The solid was then filtered off hot with suction and the filtrate was concentrated under reduced pressure, the residue was taken up in 1 N sodium hydroxide solution, the mixture was heated to 80° C. and the solid was filtered off with suction. The filtrate was brought to pH 4–5 using 2 N hydrochloric acid. The precipitate formed in this way was purified by flash chromatography on a silica gel column, dichloromethane/methanol (19/0.2). Yield:

6.55 g (68% of theory); melting point: 242° C.

$C_{25}H_{20}N_4O_2$ (MW=408.7 g/mol); mass spectrum: 409.1 (21%, M+H); 244.2 (17%); 243.2 (100%); 167.0 (17%)

b) 1-Benzyloxymethyl-3-methyl-7-tritylxanthine 1.3 g (9.44 mmol) of potassium carbonate were added at 60° C. to a solution of 2.4 g (5.9 mmol) of 3-methyl-7-tritylxanthine from stage a) in 50 ml of dimethylformamide and the mixture was stirred at this temperature for one hour. 1.06 ml (7.67 mmol) of benzyloxymethyl chloride were then added dropwise and the mixture was stirred at 80° C. for 7 hours. 50 ml of water were then added and the mixture was extracted three times using 60 ml of methyl tert-butyl ether each time. The combined organic phases were washed twice with 30 ml of water each time, dried using magnesium sulfate and concentrated under reduced pressure. The crude product was purified by flash chromatography on a silica gel column, heptane/ethyl acetate (3/2).

Yield: 1.57 g (51% of theory); melting point: 164° C.; $C_{33}H_{28}N_4O_3$ (MW=528.9 g/mol); mass spectrum: 535.2 (74%, M+Li); 243.1 (100%)

c) 1-Benzyloxymethyl-3-methylxanthine (compound 68)

A mixture of 1.1 ml of ethanol and 2.2 ml of 1 N hydrochloric acid was added to a suspension of 1.2 g (2.27 mmol) of 1,3,7-trisubstituted xanthine from stage b) in 11 ml of ethanol. The mixture was boiled under reflux for 1.5 hours and concentrated under reduced pressure, and the residue was purified by flash chromatography on a silica gel column, dichloromethane/methanol (19/0.5).

Yield: 0.6 g (92% of theory); melting point: 208° C.

$C_{14}H_{14}N_4O_3$ (MW=286.3 g/mol); mass spectrum: 287.2 (57%, M+H); 257.1 (77%); 179.(100%); 91.1 (24%)

Example 18

1-(2-(4-Chlorobenzyloxy)ethyl)-3-methylxanthine (compound 70)

a) 1-(2-(4-Chlorobenzyloxy)ethyl)-3-methyl-7-tritylxanthine 1.3 g (9.44 mmol) of potassium carbonate were added at 60° C. to a solution of 2.4 g (5.9 mmol) of 3-methyl-7-tritylxanthine (prepared according to Example 17a) in 50 ml of N-methylpyrrolidone and the mixture was stirred at this temperature for one hour. 1.57 g (7.67 mmol) of 2-(4-chlorobenzyloxy)ethyl chloride were then added dropwise and the mixture was stirred at 80° C. for one hour. A further 1.0 g (4.9 mmol) of 2-(4-chlorobenzyloxy)ethyl chloride was then added and the mixture was stirred again for one hour. 50 ml of water were then added, the mixture was extracted three times using 60 ml of methyl tert-butyl ether each time, and the combined organic phases were washed twice with 30 ml of water each time, dried using magnesium sulfate and concentrated under reduced pressure. The crude product was purified by flash chromatography on a silica gel column, heptane/ethyl acetate (3/2).

Yield: 2.13 g (63% of theory); melting point: 179° C.; $C_{34}H_{29}ClN_4O_3$ (MW=577.1 g/mol); mass spectrum: 585 (5%, $^{37}Cl$, M+Li); 583.2 (8%, $^{35}Cl$, M+Li); 243.1 (100%)

b) 1-(2-(4-Chlorobenzyloxy)ethyl)-3-methylxanthine (compound 70)

A mixture of 1.4 ml of ethanol and 2.8 ml of 1 N hydrochloric acid was added to a suspension of 1.3 g (2.26 mmol) of 1,3,7-trisubstituted xanthine from stage a) in 14 ml of ethanol. The mixture was boiled under reflux for one hour, concentrated under reduced pressure and purified by flash chromatography on a silica gel column. Dichloromethane/methanol (19/0.5).

Yield: 0.72 g (95% of theory); melting point: 152° C.

$C_{15}H_{15}ClN_4O_3$ (MW=334.7 g/mol); mass spectrum: 336 (1%, $^{37}Cl$, M); 334 (2%, $^{35}Cl$, M); 194 (100%); 179 (25%); 166 (65%)

TABLE 1

Compounds of formula I

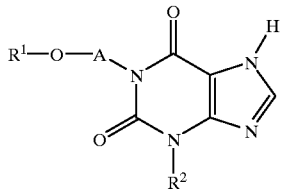

(I)

| Compound | $R^1$ | A | $R^2$ | M.p. [° C.] |
|---|---|---|---|---|
| 1 | $CH_3—$ | $—CH_2—$ | $CH_3—$ | 218 |
| 2 | $CH_3—$ | $—CH_2—$ | $CH_3—CH_2—$ | 178 |
| 3 | $CH_3—$ | $—CH_2—$ | $CH_3—(CH_2)_2—$ | 160 |
| 4 | $CH_3—$ | $—CH_2—$ | $CH_3—(CH_2)_3—$ | 160 |
| 5 | $CH_3—$ | $—CH_2—$ | cyclopropyl | 205 |
| 6 | $CH_3—$ | $—CH_2CH_2—$ | $CH_3—$ | 188 |
| 7 | $CH_3—$ | $—CH_2CH_2—$ | $CH_3—CH_2—$ | 176 |
| 8 | $CH_3—$ | $—CH_2CH_2—$ | $CH_3—(CH_2)_2—$ | 140 |
| 9 | $CH_3—$ | $—CH_2CH_2—$ | $CH_3—(CH_2)_3—$ | 115 |
| 10 | $CH_3—$ | $—CH_2CH_2—$ | cyclopropyl | 203 |
| 11 | $CH_3—$ | $—CH_2CH_2CH_2—$ | $CH_3—$ | 196 |
| 12 | $CH_3—$ | $—CH_2CH_2CH_2—$ | $CH_3—CH_2—$ | 221 |
| 13 | $CH_3—$ | $—CH_2CH_2CH_2—$ | $CH_3—(CH_2)_2—$ | 163 |
| 14 | $CH_3—$ | $—CH_2CH_2CH_2—$ | $CH_3—(CH_2)_3—$ | 157 |
| 15 | $CH_3—$ | $—CH_2CH_2CH_2—$ | cyclopropyl | 208 |
| 16 | $CH_3—CH_2—$ | $—CH_2—$ | $CH_3—$ | 198 |
| 17 | $CH_3—CH_2—$ | $—CH_2—$ | $CH_3—CH_2—$ | 176 |
| 18 | $CH_3—CH_2—$ | $—CH_2—$ | $CH_3—(CH_2)_2—$ | 134 |
| 19 | $CH_3—CH_2—$ | $—CH_2—$ | $CH_3—(CH_2)_3—$ | 129 |
| 20 | $CH_3—CH_2—$ | $—CH_2—$ | cyclopropyl | 210 |
| 21 | $CH_3—CH_2—$ | $—CH_2CH_2—$ | $CH_3—$ | 187 |
| 22 | $CH_3—CH_2—$ | $—CH_2CH_2—$ | $CH_3—CH_2—$ | 204 |
| 23 | $CH_3—CH_2—$ | $—CH_2CH_2—$ | $CH_3—(CH_2)_2—$ | 153 |
| 24 | $CH_3—CH_2—$ | $—CH_2CH_2—$ | $CH_3—(CH_2)_3—$ | 136 |
| 25 | $CH_3—CH_2—$ | $—CH_2CH_2—$ | cyclopropyl | 214 |
| 26 | $CH_3—(CH_2)_2—$ | $—CH_2—$ | $CH_3—$ | 156 |
| 27 | $CH_3—(CH_2)_2—$ | $—CH_2—$ | $CH_3—CH_2—$ | 159 |
| 28 | $CH_3—(CH_2)_2—$ | $—CH_2—$ | $CH_3—(CH_2)_2—$ | 122 |
| 29 | $CH_3—(CH_2)_2—$ | $—CH_2—$ | $(CH_3)_2—CH—$ | 152 |
| 30 | $CH_3—(CH_2)_2—$ | $—CH_2—$ | $CH_3—(CH_2)_3—$ | 119 |
| 31 | $CH_3—(CH_2)_2—$ | $—CH_2—$ | $(CH_3)_2—CH—CH_2—$ | 141 |

TABLE 1-continued

Compounds of formula I

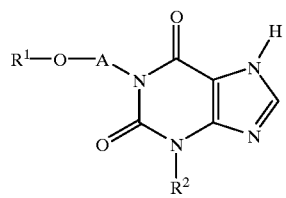

(I)

| Compound | R¹ | A | R² | M.p. [° C.] |
|---|---|---|---|---|
| 32 | CH₃—(CH₂)₂— | —CH₂— | (phenyl) | 220 |
| 33 | CH₃—(CH₂)₂— | —CH₂— | (cyclopropyl) | 197 |
| 34 | CH₃—(CH₂)₂— | —CH₂— | (cyclopropylmethyl) | 132 |
| 35 | CH₃—(CH₂)₂— | —CH₂CH₂— | CH₃— | 174 |
| 36 | CH₃—(CH₂)₂— | —CH₂CH₂— | CH₃—CH₂— | 192 |
| 37 | CH₃—(CH₂)₂— | —CH₂CH₂— | CH₃—(CH₂)₂— | 137 |
| 38 | CH₃—(CH₂)₂— | —CH₂CH₂— | CH₃—(CH₂)₃— | 138 |
| 39 | CH₃—(CH₂)₂— | —CH₂CH₂— | (cyclopropyl) | 202 |
| 40 | CH₃—(CH₂)₃— | —CH₂— | CH₃— | 130 |
| 41 | CH₃—(CH₂)₃— | —CH₂— | CH₃—CH₂— | 144 |
| 42 | CH₃—(CH₂)₃— | —CH₂— | (CH₃)₂—CH— | 131 |
| 43 | CH₃—(CH₂)₃— | —CH₂CH₂— | CH₃— | 159 |
| 44 | CH₃—(CH₂)₃— | —CH₂CH₂— | CH₃—CH₂— | 165 |
| 45 | CH₃—(CH₂)₃— | —CH₂CH₂— | CH₃—(CH₂)₂— | 116 |
| 46 | CH₃—(CH₂)₃— | —CH₂CH₂— | CH₃—(CH₂)₃— | 119 |
| 47 | CH₃—(CH₂)₃— | —CH₂CH₂— | (cyclopropyl) | 160 |
| 48 | (CH₃)₂—CH—CH₂— | —CH₂— | CH₃— | 160 |
| 49 | (CH₃)₂—CH—CH₂— | —CH₂— | CH₃—CH₂— | 182 |
| 50 | (CH₃)₂—CH—CH₂— | —CH₂— | (cyclopropyl) | 181 |
| 51 | CH₃—CH₂—CH(CH₃)— | —CH₂— | CH₃— | 175 |
| 52 | CH₃CH₂CH(CH₃)— | —CH₂— | CH₃—CH₂— | 189 |
| 53 | CH₃—O—(CH₂)₂— | —CH₂— | CH₃— | 188 |
| 54 | CH₃—O—(CH₂)₂— | —CH₂— | CH₃—CH₂— | 166 |
| 55 | CH₃—O—(CH₂)₂— | —CH₂CH₂— | CH₃— | 121 |
| 56 | CH₃—O—(CH₂)₂— | —CH₂CH₂— | CH₃—CH₂— | 140 |
| 57 | (phenyl) | —CH₂— | CH₃— | 190 |
| 58 | (phenyl) | —CH₂— | CH₃—CH₂— | 196 |

TABLE 1-continued
Compounds of formula I
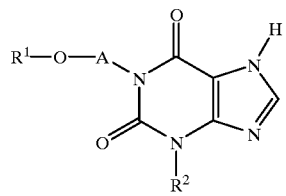
(I)
| Compound | R¹ | A | R² | M.p. [° C.] |
|---|---|---|---|---|
| 59 | phenyl | —CH₂— | $CH_3-(CH_2)_3-$ | 139 |
| 60 | phenyl | —CH₂CH₂— | $CH_3-$ | 207 |
| 61 | phenyl | —CH₂CH₂— | $CH_3-CH_2-$ | 221 |
| 62 | phenyl | —CH₂CH₂— | $CH_3-(CH_2)_2-$ | 176 |
| 63 | phenyl | —CH₂CH₂— | $CH_3-(CH_2)_3-$ | 121 |
| 64 | phenyl | —CH₂CH₂— | cyclopropyl | 236 |
| 65 | 4-chlorophenyl | —CH₂— | $CH_3-$ | 218 |
| 66 | 4-chlorophenyl | —CH₂— | $CH_3-CH_2-$ | 205 |
| 67 | 4-chlorophenyl | —CH₂— | $CH_3-(CH_2)_3-$ | 169 |
| 68 | benzyl (phenyl-CH₂CH₂) | —CH₂— | $CH_3-$ | 208 |

TABLE 1-continued

Compounds of formula I

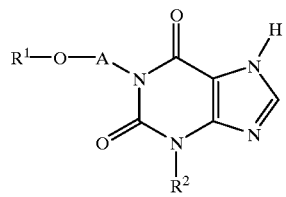

(I)

| Compound | $R^1$ | A | $R^2$ | M.p. [° C.] |
|---|---|---|---|---|
| 69 | benzyl | —$CH_2$— | $CH_3$—$CH_2$— | 142 |
| 70 | 4-chlorobenzyl | —$CH_2CH_2$— | $CH_3$— | 152 |

M.p. is the abbreviation for melting point.

TABLE 2

Intermediates of formula VIII ($R^a$ = benzyl)

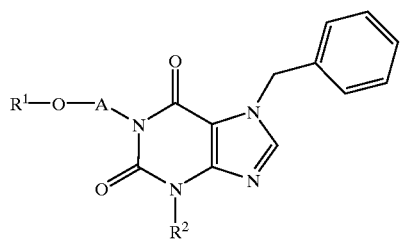

(VIII)

| Compound | $R^1$ | A | $R^2$ | M.p. [° C.] |
|---|---|---|---|---|
| 71 | $CH_3$— | —$CH_2$— | $CH_3$— | 114 |
| 72 | $CH_3$— | —$CH_2$— | $CH_3$—$CH_2$— | 124 |
| 73 | $CH_3$— | —$CH_2$— | $CH_3$—$(CH_2)_2$— | 134 |
| 74 | $CH_3$— | —$CH_2$— | $CH_3$—$(CH_2)_3$— | 93 |
| 75 | $CH_3$— | —$CH_2$— | cyclopropyl | 141 |
| 76 | $CH_3$— | —$CH_2CH_2$— | $CH_3$— | 90 |
| 77 | $CH_3$— | —$CH_2CH_2$— | $CH_3$—$CH_2$— | 90 |
| 78 | $CH_3$— | —$CH_2CH_2$— | $CH_3$—$(CH_2)_2$— | 99 |
| 79 | $CH_3$— | —$CH_2CH_2$— | $CH_3$—$(CH_2)_3$— | oil |
| 80 | $CH_3$— | —$CH_2CH_2$— | cyclopropyl | 117 |
| 81 | $CH_3$— | —$CH_2CH_2CH_2$— | $CH_3$— | 89 |
| 82 | $CH_3$— | —$CH_2CH_2CH_2$— | $CH_3$—$CH_2$— | 92 |
| 83 | $CH_3$— | —$CH_2CH_2CH_2$— | $CH_3$—$(CH_2)_2$— | 91 |
| 84 | $CH_3$— | —$CH_2CH_2CH_2$— | $CH_3$—$(CH_2)_3$— | oil |
| 85 | $CH_3$— | —$CH_2CH_2CH_2$— | cyclopropyl | 86 |
| 86 | $CH_3$—$CH_2$— | —$CH_2$— | $CH_3$— | 103 |

TABLE 2-continued

Intermediates of formula VIII (R$^a$ = benzyl)

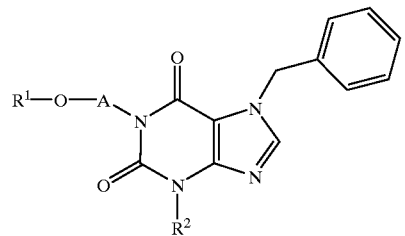

(VIII)

| Compound | R$^1$ | A | R$^2$ | M.p. [° C.] |
|---|---|---|---|---|
| 87 | CH$_3$—CH$_2$— | —CH$_2$— | CH$_3$—CH$_2$— | 91 |
| 88 | CH$_3$—CH$_2$— | —CH$_2$— | CH$_3$—(CH$_2$)$_2$— | 110 |
| 89 | CH$_3$—CH$_2$— | —CH$_2$— | CH$_3$—(CH$_2$)$_3$— | oil |
| 90 | CH$_3$—CH$_2$— | —CH$_2$— | cyclopropyl | 112 |
| 91 | CH$_3$—CH$_2$— | —CH$_2$CH$_2$— | CH$_3$— | 112 |
| 92 | CH$_3$—CH$_2$— | —CH$_2$CH$_2$— | CH$_3$—CH$_2$— | 125 |
| 93 | CH$_3$—CH$_2$— | —CH$_2$CH$_2$— | CH$_3$—(CH$_2$)$_2$— | 84 |
| 94 | CH$_3$—CH$_2$— | —CH$_2$CH$_2$— | CH$_3$—(CH$_2$)$_3$— | oil |
| 95 | CH$_3$—CH$_2$— | —CH$_2$CH$_2$— | cyclopropyl | 110 |
| 96 | CH$_3$—(CH$_2$)$_2$— | —CH$_2$— | CH$_3$— | 109 |
| 97 | CH$_3$—(CH$_2$)$_2$— | —CH$_2$— | CH$_3$—CH$_2$— | 92 |
| 98 | CH$_3$—(CH$_2$)$_2$— | —CH$_2$— | CH$_3$—(CH$_2$)$_2$— | 82 |
| 99 | CH$_3$—(CH$_2$)$_2$— | —CH$_2$— | (CH$_3$)$_2$—CH— | 95 |
| 100 | CH$_3$—(CH$_2$)$_2$— | —CH$_2$— | CH$_3$—(CH$_2$)$_3$— | oil |
| 101 | CH$_3$—(CH$_2$)$_2$— | —CH$_2$— | (CH$_3$)$_2$—CH—CH$_2$— | 72 |
| 102 | CH$_3$—(CH$_2$)$_2$— | —CH$_2$— | phenyl | 103 |
| 103 | CH$_3$—(CH$_2$)$_2$— | —CH$_2$— | cyclopropyl | 90 |
| 104 | CH$_3$—(CH$_2$)$_2$— | —CH$_2$— | cyclopropylmethyl | 88 |
| 105 | CH$_3$—(CH$_2$)$_2$— | —CH$_2$CH$_2$— | CH$_3$— | 88 |
| 106 | CH$_3$—(CH$_2$)$_2$— | —CH$_2$CH$_2$— | CH$_3$—CH$_2$— | 97 |
| 107 | CH$_3$—(CH$_2$)$_2$— | —CH$_2$CH$_2$— | CH$_3$—(CH$_2$)$_2$— | 55 |
| 108 | CH$_3$—(CH$_2$)$_2$— | —CH$_2$CH$_2$— | CH$_3$—(CH$_2$)$_3$— | oil |
| 109 | CH$_3$—(CH$_2$)$_2$— | —CH$_2$CH$_2$— | cyclopropyl | 88 |
| 110 | CH$_3$—(CH$_2$)$_3$— | —CH$_2$— | CH$_3$— | 72 |
| 111 | CH$_3$—(CH$_2$)$_3$— | —CH$_2$— | CH$_3$—CH$_2$— | 74 |
| 112 | CH$_3$—(CH$_2$)$_3$— | —CH$_2$— | (CH$_3$)$_2$—CH— | oil |
| 113 | CH$_3$—(CH$_2$)$_3$— | —CH$_2$CH$_2$— | CH$_3$— | oil |
| 114 | CH$_3$—(CH$_2$)$_3$— | —CH$_2$CH$_2$— | CH$_3$—CH$_2$— | 67 |
| 115 | CH$_3$—(CH$_2$)$_3$— | —CH$_2$CH$_2$— | CH$_3$—(CH$_2$)$_2$— | 70 |
| 116 | CH$_3$—(CH$_2$)$_3$— | —CH$_2$CH$_2$— | CH$_3$—(CH$_2$)$_3$— | oil |
| 117 | CH$_3$—(CH$_2$)$_3$— | —CH$_2$CH$_2$— | cyclopropyl | 75 |
| 118 | (CH$_3$)$_2$—CH—CH$_2$— | —CH$_2$— | CH$_3$— | 76 |

TABLE 2-continued

Intermediates of formula VIII (R$^a$ = benzyl)

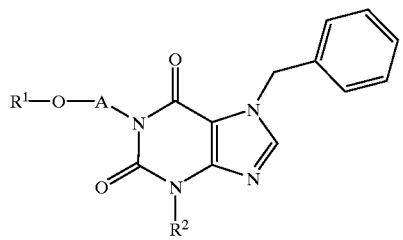

(VIII)

| Compound | R$^1$ | A | R$^2$ | M.p. [° C.] |
|---|---|---|---|---|
| 119 | (CH$_3$)$_2$—CH—CH$_2$— | —CH$_2$— | CH$_3$—CH$_2$— | 92 |
| 120 | (CH$_3$)$_2$—CH—CH$_2$— | —CH$_2$— | cyclopropyl | 99 |
| 121 | CH$_3$—CH$_2$—CH(CH$_3$)— | —CH$_2$— | CH$_3$— | oil |
| 122 | CH$_3$—CH$_2$—CH(CH$_3$)— | —CH$_2$— | CH$_3$—CH$_2$— | oil |
| 123 | CH$_3$—O—(CH$_2$)$_2$— | —CH$_2$— | CH$_3$— | oil |
| 124 | CH$_3$—O—(CH$_2$)$_2$— | —CH$_2$— | CH$_3$—CH$_2$— | oil |
| 125 | CH$_3$—O—(CH$_2$)$_2$— | —CH$_2$CH$_2$— | CH$_3$— | 78 |
| 126 | CH$_3$—O—(CH$_2$)$_2$— | —CH$_2$CH$_2$— | CH$_3$—CH$_2$— | 64 |
| 127 | phenyl | —CH$_2$CH$_2$— | CH$_3$— | 141 |
| 128 | phenyl | —CH$_2$CH$_2$— | CH$_3$—CH$_2$— | 125 |
| 129 | phenyl | —CH$_2$CH$_2$— | CH$_3$—(CH$_2$)$_2$— | 94 |
| 130 | phenyl | —CH$_2$CH$_2$— | CH$_3$—(CH$_2$)$_3$— | 122 |
| 131 | phenyl | —CH$_2$CH$_2$— | cyclopropyl | 150 |
| 132 | 4-Cl-phenyl | —CH$_2$— | CH$_3$— | 96 |
| 133 | 4-Cl-phenyl | —CH$_2$— | CH$_3$—CH$_2$— | 119 |

TABLE 2-continued

Intermediates of formula VIII ($R^a$ = benzyl)

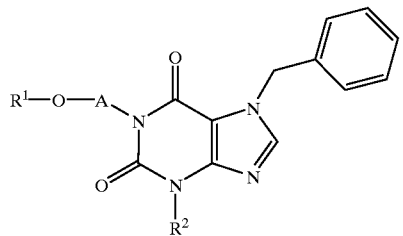

(VIII)

| Compound | $R^1$ | A | $R^2$ | M.p. [° C.] |
|---|---|---|---|---|
| 134 | 4-Cl-C$_6$H$_4$-CH$_2$- | —CH$_2$— | CH$_3$—(CH$_2$)$_3$— | oil |

Pharmacological Testing and Results

The pronounced antishock action of the compounds of formula I was demonstrated in the well-established model of endotoxin (LPS)-induced lethal shock on C57BL/6 mice by means of the decrease in mortality.

To carry out the experiments, a mixture of 10 ng of LPS from Salmonella abortus equi. and 7.5 mg of galactosamine in 0.2 ml of phosphate-buffered, physiological saline solution was administered to each animal by intravenous injection, which as a rule led to death within 6 to 9 hours. The test preparations were administered intraperitoneally one hour before LPS provocation at a dose of 100 mg/kg. The animals of the control group (n=10) instead of this received pure 0.9% saline solution as placebo. To assess the action of the preparation, the number of surviving animals was determined in the treated group (n=10) 48 hours after LPS administration and from this the percentage inhibition of mortality was determined with respect to the mortality in the control group. The experimental results are Table 3.

TABLE 3

Inhibition of LPS-induced mortality in the mouse

| Compound from Table 1 | Inhibition of mortality in % |
|---|---|
| 1 | 80 |
| 2 | 30 |
| 4 | 30 |
| 8 | 30 |
| 16 | 100 |
| 17 | 100 |
| 21 | 40 |
| 23 | 40 |
| 26 | 100 |
| 27 | 100 |
| 29 | 50 |
| 31 | 30 |
| 32 | 90 |
| 34 | 30 |
| 35 | 30 |
| 37 | 80 |
| 39 | 30 |
| 40 | 40 |
| 41 | 40 |
| 44 | 30 |
| 48 | 40 |
| 50 | 40 |

TABLE 3-continued

Inhibition of LPS-induced mortality in the mouse

| Compound from Table 1 | Inhibition of mortality in % |
|---|---|
| 52 | 30 |
| 54 | 30 |

In the course of wider pharmacological screening, it was additionally possible to show that the compounds of the formula I were additionally able to inhibit ischemically-related cell death in the central nervous system in a lasting manner. They are therefore also suitable for the treatment and prophylaxis of cerebrovascular disorders, such as stroke; transitory ischemic attacks (TIA); multiinfarct dementia; dementia of the mixed type with a vascular and degenerative (Alzheimer) component; spinal cord damage; cerebral trauma as a result of head injuries; and neuronal damage after cardiac arrest, (neonatal) asphyxia and reanimation as well as vascular surgical interventions (e.g. bypass operations) in the area of the main arteries supplying the brain.

It was convincingly possible to demonstrate the neuronal protective action of the theophylline derivatives according to formula I, inter alia, in the model of transient global ischemia in the gerbil. This finding is also surprising inasmuch as theophylline itself under comparable experimental conditions inhibits ischemic nerve cell damage neither in the gerbil (J. Cereb. Blood Flow Metab. 1987, 7/1: 74–81) nor the rat (J. Cereb. Blood Flow Metab. 1994, 14/1: 166–173), but rather increases it even more.

To carry out the experiment, which took place according to the guidelines of the German Animal Protection Act, 30 male Mongolian gerbils having a body weight of between 60 and 70 g were randomly divided into two groups each containing 15 animals. The respective test substance was administered to the animals of the first group 30 minutes after the ischemia period by intraperitoneal injection, while the animals of the second group, which served as an untreated control group, only received the same volume of the vehicle concerned. To produce the temporary forebrain ischemia, the animals were fixed in the supine position to a heated operated table, and both common carotid arteries were carefully exposed and closed for 3 minutes by means of microaneurysm clips. 7 days after the 3-minute ischemia period, the animals were decapitated under halothane anesthesia, the brains were rapidly and carefully removed, first fixed by immersion in Carnoy's solution (ethanol/chloroform/acetic acid=6/3/1) and then embedded in paraffin. Subsequently 4 to 6 μm thick coronal sections through the hippocampus were prepared approximately at the height of the bregma and these were stained with hematoxylin and eosin. After this, the extent of eosinophilic necrosis of the pyramidal cells in the CA1 region of the hippocampus was determined by light microscopy in the course of a blind experiment by means of a semiquantitative histopathological score (0=none; 1=slight; 2=medium severe; 3=severe and 4=complete necroses). The assessment variable used for the neuroprotective action was the percentage change in the mean histopathological score of the preparation group compared to that of the untreated control group. The experimental results are compiled in Table 4.

TABLE 4

Inhibition of ischemic nerve cell damage in the Mongolian gerbil

| Compound from Table 1 or 2 | Dose in mg/kg | Inhibition of the neuronal CA1 hippocampus damage in % |
|---|---|---|
| 5 | 10 | 20 |
| 6 | 10 | 20 |
| 7 | 10 | 33 |
| 17 | 10 | 66 |
| 24 | 10 | 30 |
| 25 | 10 | 24 |
| 27 | 10 | 67 |
| 27 | 5 | 40 |
| 28 | 10 | 30 |
| 30 | 10 | 24 |
| 36 | 10 | 23 |
| 39 | 10 | 36 |
| 44 | 10 | 64 |
| 54 | 10 | 36 |
| 58 | 10 | 20 |
| 61 | 10 | 23 |
| 63 | 10 | 27 |
| 66 | 10 | 23 |
| 77 | 10 | 33 |
| 82 | 10 | 30 |
| 103 | 10 | 32 |
| 114 | 10 | 27 |

What is claimed is:

1. A compound of the formula I

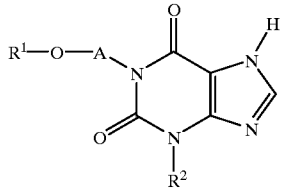

(I)

or a physiologically tolerable salt thereof, or a stereoisomeric form of the compound of formula I, where $R^1$ is
a) straight-chain or branched $(C_1-C_5)$-alkyl,
b) $(C_1-C_2)$-alkoxy-$(C_1-C_3)$-alkyl, or
c) phenyl or phenyl-$(C_1-C_2)$-alkyl, in which the phenyl radicals are unsubstituted or each substituted by one or two halogen atoms, A is an unbranched or branched $(C_1-C_4)$-alkylene bridge and $R^2$ is
a) straight-chain or branched $(C_1-C_4)$-alkyl,
b) $(C_3-C_6)$-cycloalkyl,
c) $(C_4-C_8)$-cycloalkylalkyl,
d) phenyl or
e) phenyl-$(C_1-C_2)$-alkyl, where compounds of the formula I in which a) $R^2$ is n-propyl, $R^1$ is methyl or ethyl and A is an ethylene bridge or b) $R^2$ is n-propyl, $R^1$ is methyl and A is an n-propylene bridge, are excluded.

2. A compound of the formula I as claimed in claim 1, where $R^1$ is
a) straight-chain or branched $(C_1-C_4)$-alkyl,
b) methoxymethyl,
c) methoxyethyl,
d) phenyl,
e) 4-chlorophenyl,
f) benzyl or
g) 4-chlorobenzyl, A is an unbranched $(C_1-C_3)$-alkylene bridge and $R^2$ is
a) straight-chain or branched $(C_1-C_4)$-alkyl,
b) cyclopropyl,
c) cyclopropylmethyl,
d) phenyl or
e) benzyl.

3. A compound of the formula I as claimed in claims 1 or 2, where $R^1$ is straight-chain or branched $(C_1-C_4)$-alkyl, A is an unbranched $(C_1-C_3)$-alkylene bridge and $R^2$ is straight-chain or branched $(C_1-C_4)$-alkyl, cyclopropyl or cyclopropylmethyl.

4. The compound according to claim 1 which is 1-methoxymethyl-3-methylxathine.

5. The compound according to claim 1 which is 3-cyclopropyl-1-(2-methoxyethyl)xanthine.

6. The compound according to claim 1 which is 3-butyl-1-(3-methoxypropyl)xanthine.

7. The compound according to claim 1 which is 1-ethoxymethyl-3-propylxanthine.

8. The compound according to claim 1 which is 3-ethyl-1-propoxymethylxanthine.

9. The compound according to claim 1 which is 3-isobutyl-1-propoxymethylxanthine.

10. The compound according to claim 1 which is 3-phenyl-1-propoxymethylxanthine.

11. The compound according to claim 1 which is 3-cyclopropylmethyl-1-propoxymethylxanthine.

12. The compound according to claim 1 which is 1-(2-propoxyethyl)-3-propylxanthine.

13. The compound according to claim 1 which is 1-butoxymethyl-3-isopropylxanthine.

14. The compound according to claim 1 which is 1-isobutoxymethyl-3-methylxanthine.

15. The compound according to claim 1 which is 1-sec-butoxymethyl-3-ethylxanthine.

16. The compound according to claim 1 which is 1-(2-methoxyethoxymethyl)-3-methylxanthine.

17. The compound according to claim 1 which is 3-ethyl-1-(2-(2-methoxyethoxy)ethyl)xanthine.

18. The compound according to claim 1 which is 3-methyl-1-(2-phenoxyethyl)xanthine.

19. The compound according to claim 1 which is 1-(chlorophenoxymethyl)-3-methylxanthine.

20. The compound according to claim 1 which is 1-benzloxymethyl-3-methylxanthine.

21. The compound according to claim 1 which is 1-(2-(4-chlorobenzyoxy)ethyl)-3-methylxanthine.

22. A pharmaceutical composition comprising a therapeutically effective amount of at least one compound of the formula I as claimed in claim 1 in admixture with a pharmaceutically acceptable and physiologically tolerable excipient and/or an additive, a diluent, or an auxiliary.

23. A process for the preparation of the compound of the formula I as claimed in claim 1, which comprises a) reacting without a condensing agent or in the presence of a basic condensing agent, a 3-substituted xanthine of the formula II or a salt of formula II

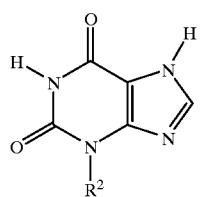

(II)

wherein $R^2$ is a straight-chain or branched ($C_1$–$C_5$)-alkyl, ($C_3$–$C_6$)-cycloalkyl, ($C_4$–$C_8$)-cycloalkylalkyl, phenyl, or phenyl-($C_1$–$C_2$)-alkyl, with a reagent of the formula III $R^a$—X  (III)

wherein $R^a$ is a benzyl, benzhydryl, or trityl group, and X is chlorine, bromine, or iodine; or b) reacting without a condensing agent or in the presence of a basic condensing agent, a 7-substituted xanthine of the formula IV or a salt of formula IV

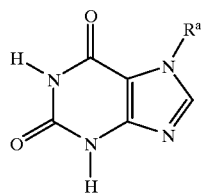

(IV)

wherein $R^a$ is a benzyl, benzhydryl, or trityl group, with a reagent of the formula V $R^2$—X  (V)

wherein $R^2$ is a straight-chain or branched ($C_1$–$C_5$)-alkyl, ($C_3$–$C_6$)-cycloalkyl, ($C_4$–$C_8$)-cycloalkylalkyl, phenyl, or phenyl-($C_1$–$C_2$)-alkyl, and X is chlorine, bromine, or iodine, to give a 3,7-disubstituted xanthine of the formula VI

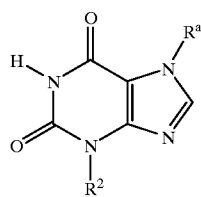

(VI)

wherein $R^2$ and $R^a$ are as defined above; then, reacting without condensing agent or in the presence of a basic condensing agent, the compound of the formula VI or a salt of formula VI with an alkylating agent of the formula VII $R^1$—O—A—X  (VII)

wherein $R^1$ is a straight-chain or branched ($C_1$–$C_5$)-alkyl, ($C_1$–$C_2$)-alkoxy-($C_1$–$C_3$)-alkyl, or phenyl or phenyl-($C_1$–$C_2$)-alkyl, wherein the phenyl group is unsubstituted or substituted by one or two halogen atoms, A is an unbranched or branched ($C_1$–$C_4$)-alkylene bridge, and X is chlorine, bromine, or iodine, to give a 1,3,7-trisubstituted xanthine of the formula VIII

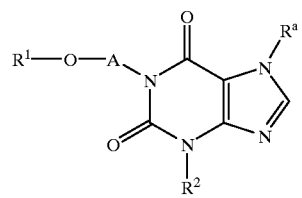

(VIII)

wherein $R^1$, A, $R^2$, and $R^a$ are as defined above, and then, removing $R^a$ from formula VIII to give a compound of the formula I; and optionally converting formula I into a physiologically tolerable salt.

24. A compound of the formula VIII

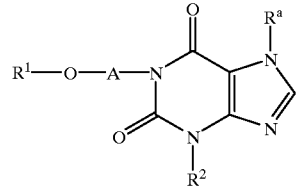

(VIII)

or a physiologically tolerable salt thereof, or a stereoisomeric form of the compound of formula VIII, wherein $R^1$ is a) straight-chain or branched ($C_1$–$C_5$)-alkyl,
b) ($C_1$–$C_2$)-alkoxy-($C_1$–$C_2$)-alkyl, or
c) phenyl or phenyl-($C_1$–$C_2$)-alkyl, wherein the phenyl group is unsubstituted or each phenyl group is substituted with one or two halogen atoms;

A is an unbranched or branched ($C_1$–$C_4$)-alkylene bridge;

$R^2$ is a) straight-chain or branched ($C_1$–$C_5$)-alkyl,
b) ($C_3$–$C_6$)-cycloalkyl,
c) ($C_4$–$C_8$)-cycloalkylalkyl,
d) phenyl, or
e) phenyl-($C_1$–$C_2$)-alkyl; and $R^a$ is benzyl.

* * * * *

UNITED STATES PATENT AND TRADEMARK OFFICE
CERTIFICATE OF CORRECTION

PATENT NO.    : 6,214,992 B1
DATED         : April 10, 2001
INVENTOR(S)   : Ulrich Gebert et al.

It is certified that error appears in the above-identified patent and that said Letters Patent is hereby corrected as shown below:

<u>Column 40, claim 1,</u>
Line 2, "$(C_1-C_4)$-alkyl" should read -- $(C_1-C_5)$-alkyl --.

Signed and Sealed this

Twenty-sixth Day of February, 2002

Attest:

JAMES E. ROGAN
*Attesting Officer*  *Director of the United States Patent and Trademark Office*